US012228540B2

(12) United States Patent
Yang et al.

(10) Patent No.: US 12,228,540 B2
(45) Date of Patent: Feb. 18, 2025

(54) BIOCHEMICAL TEST CHIP

(71) Applicant: APEX BIOTECHNOLOGY CORP., Hsinchu (TW)

(72) Inventors: Chen-Yu Yang, Toufen (TW); Cheng-Yu Chou, Miaoli County (TW)

(73) Assignee: APEX BIOTECHNOLOGY CORP., Hsinchu (TW)

( * ) Notice: Subject to any disclaimer, the term of this patent is extended or adjusted under 35 U.S.C. 154(b) by 256 days.

(21) Appl. No.: 17/339,599

(22) Filed: Jun. 4, 2021

(65) Prior Publication Data

US 2022/0163476 A1    May 26, 2022

(30) Foreign Application Priority Data

Nov. 25, 2020   (TW) .................................. 109141391

(51) Int. Cl.
*G01N 27/327*   (2006.01)
*C12Q 1/00*     (2006.01)

(52) U.S. Cl.
CPC ......... *G01N 27/3272* (2013.01); *C12Q 1/001* (2013.01)

(58) Field of Classification Search
CPC ...... C12Q 1/001; G01N 27/27; G01N 27/327; G01N 27/307; G01N 27/3271; G01N 27/3272
See application file for complete search history.

(56) References Cited

U.S. PATENT DOCUMENTS

| | | | |
|---|---|---|---|
| 3,380,905 A | 4/1968 | Clark, Jr. | |
| 4,287,027 A | 9/1981 | Tosk | |
| 4,571,292 A | 2/1986 | Liu et al. | |
| 4,670,127 A | 6/1987 | Ritter et al. | |
| 4,725,422 A | 2/1988 | Miyabayashi et al. | |
| 4,897,173 A | 1/1990 | Nankai et al. | |
| 4,970,145 A | 11/1990 | Bennetto et al. | |

(Continued)

FOREIGN PATENT DOCUMENTS

| EP | 1343007 A1 | 9/2003 |
|---|---|---|
| EP | 4006534 A1 | 6/2022 |

(Continued)

OTHER PUBLICATIONS

Extended European Search report from the EPO counterpart application EP21191424, dated Jan. 31, 2022, 9 pages.

(Continued)

*Primary Examiner* — Gurpreet Kaur
(74) *Attorney, Agent, or Firm* — MUNCY, GEISSLER, OLDS & LOWE, P.C.

(57) ABSTRACT

The present disclosure provides a biochemical test chip, including an insulating substrate, an electrode unit, a first insulating septum, a reactive layer and a second insulating septum. The electrode unit is located on the insulating substrate. The electrode unit includes a working electrode and a counter electrode. A current density of the counter electrode is greater than a current density of the working electrode. The first insulating septum is located on the electrode unit. The first insulating septum has an opening, which at least partially exposes the electrode unit. The reactive layer is located in the opening and is electrically connected to the electrode unit. The second insulating septum is located on the first insulating septum.

9 Claims, 14 Drawing Sheets

(56) References Cited

U.S. PATENT DOCUMENTS

| | | | |
|---|---|---|---|
| 4,978,600 A | 12/1990 | Suzuki et al. | |
| 5,030,310 A | 7/1991 | Wogoman | |
| 5,231,028 A | 7/1993 | Mullen | |
| 5,262,035 A | 11/1993 | Gregg et al. | |
| 5,288,636 A | 2/1994 | Pollmann et al. | |
| 5,508,171 A | 4/1996 | Walling et al. | |
| 5,630,919 A | 5/1997 | Chang | |
| 5,820,551 A | 10/1998 | Hill et al. | |
| 5,942,102 A | 8/1999 | Hodges et al. | |
| 6,153,069 A | 11/2000 | Pottgen et al. | |
| 6,299,757 B1 | 10/2001 | Feldman et al. | |
| 6,413,411 B1 | 7/2002 | Pottgen et al. | |
| 6,491,803 B1 | 12/2002 | Shen et al. | |
| 6,592,745 B1 | 7/2003 | Feldman et al. | |
| 6,632,349 B1 | 10/2003 | Hodges et al. | |
| 6,685,196 B1 | 2/2004 | Baerveldt | |
| 6,875,327 B1* | 4/2005 | Miyazaki | G01N 33/48771 204/406 |
| 6,885,196 B2* | 4/2005 | Taniike | G01N 27/3272 324/438 |
| 6,892,085 B2 | 5/2005 | McIvor et al. | |
| 6,960,289 B2 | 11/2005 | Hodges et al. | |
| RE42,567 E | 7/2011 | Hodges et al. | |
| 8,075,760 B2 | 12/2011 | Hodges et al. | |
| 2001/0006149 A1* | 7/2001 | Taniike | C12Q 1/004 204/403.08 |
| 2002/0179457 A1 | 12/2002 | Heller | |
| 2003/0032875 A1 | 2/2003 | Taniike et al. | |
| 2004/0007461 A1 | 1/2004 | Edelbrock et al. | |
| 2005/0287035 A1 | 12/2005 | Yon-Hin et al. | |
| 2006/0037870 A1* | 2/2006 | Deng | C12Q 1/54 205/777.5 |
| 2007/0213611 A1 | 9/2007 | Simpson et al. | |
| 2009/0297836 A1 | 12/2009 | Douglas | |
| 2010/0012521 A1 | 1/2010 | Feldman et al. | |
| 2010/0012522 A1 | 1/2010 | Feldman et al. | |
| 2010/0252450 A1 | 10/2010 | Riehl et al. | |
| 2011/0144466 A1 | 6/2011 | Zhang | |
| 2012/0132540 A1* | 5/2012 | Wang | G01N 27/3274 204/403.01 |
| 2012/0181189 A1* | 7/2012 | Merchant | C12Q 1/001 204/403.14 |
| 2017/0285016 A1 | 10/2017 | Musho et al. | |
| 2018/0100826 A1* | 4/2018 | Marquant | G01N 27/301 |
| 2018/0187249 A1 | 7/2018 | Su et al. | |
| 2020/0024632 A1 | 1/2020 | Wu et al. | |

FOREIGN PATENT DOCUMENTS

| | | |
|---|---|---|
| JP | 2005-17233 A | 1/2005 |
| TW | I512287 | 12/2015 |
| TW | I582418 | 5/2017 |

OTHER PUBLICATIONS

Office action and search report dated Nov. 29, 2021 from the TIPO counterpart application TW109141391, with brief translation thereof, 5 pages.
Office action dated Aug. 21, 2023 from the CNIPA counterpart application 202110260448.7.
Brief translation of the Office action dated Aug. 21, 2023 from the CNIPA counterpart application 202110260448.7.
Communication from EPO—Search report dated Sep. 28, 2023.
European communication dated May 16, 2024 from the EPO counterpart application EP21191424.
Office action dated Jan. 19, 2024 from the CNIPA counterpart application 202110260448.7.
Brief translation of the Office action dated Jan. 19, 2024 from the CNIPA counterpart application 202110260448.7.
An office action of the counterpart Taiwan application No. 112114281 from TIPO with translation, Dec. 23, 2024.

* cited by examiner

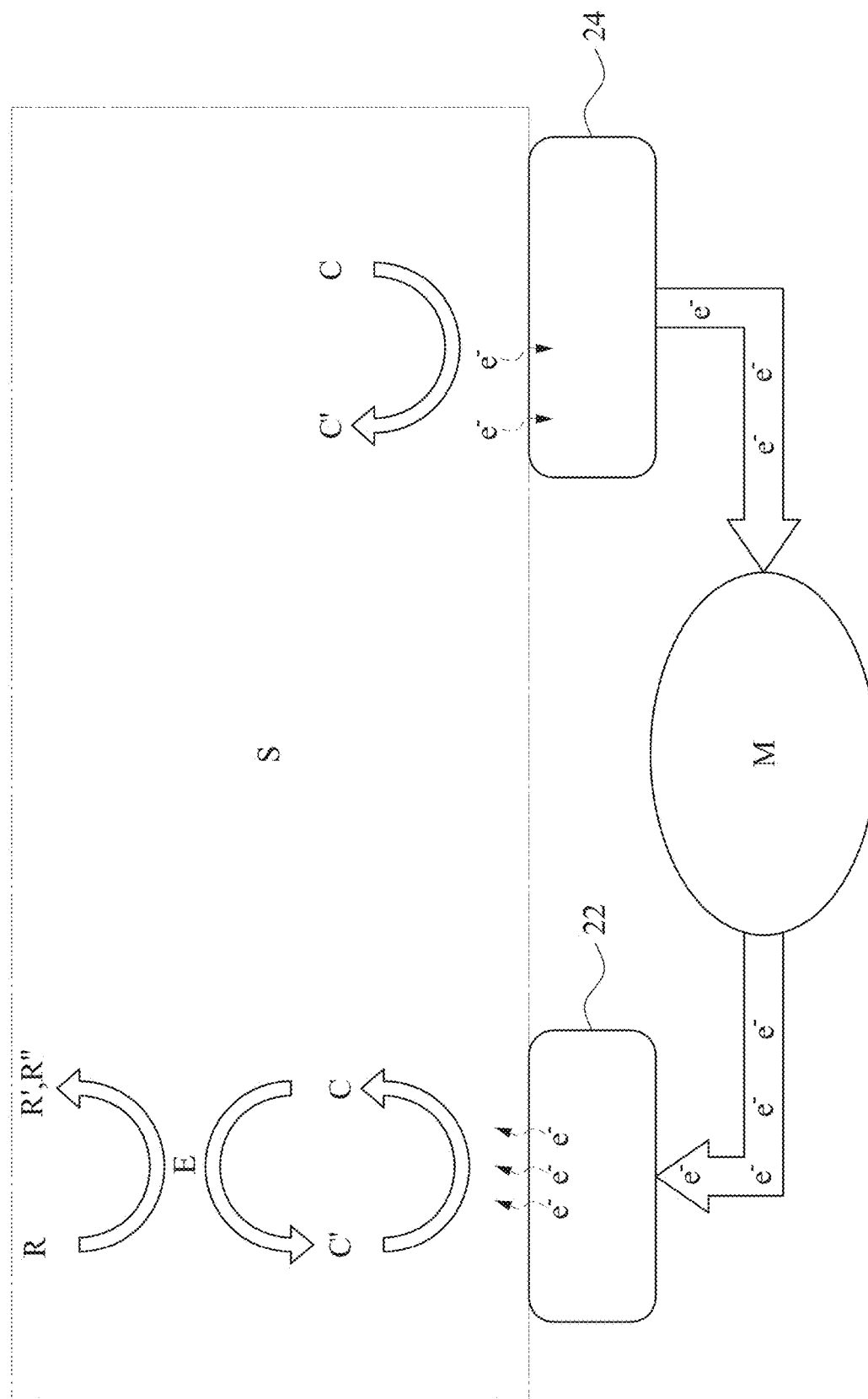

BIOCHEMICAL TEST CHIP

CROSS-REFERENCE TO RELATED APPLICATIONS

This application claims the benefits of Taiwan Patent Application No. 109141391, filed on Nov. 25, 2020, which is hereby incorporated herein by reference in its entirety.

TECHNICAL FIELD

The present application relates to a biochemical test chip for use in medical measurement, particularly to a biochemical test chip capable of increasing the electrical neutrality of a counter electrode.

BACKGROUND

In-vitro medical measurement plays a vital role in today's medical industry; by qualitatively and quantitatively measuring biological fluids changes, it provides index information for rapid diagnosis and treatment of diseases. The use of biochemical test chips has become a standard technique for medical or biochemical testing.

Conventional biochemical test chips have at least two electrodes. After loading the specimen into the biochemical test chip's reaction zone, the electrochemical properties of the specimen can be measured using said two electrodes. When the specimen undergoes an electrochemical reaction, a change in current occurs, and this current change is linearly proportional to the concentration of substances in the specimen that can undergo the redox reaction. Therefore, one can analyze the specimen's concentration by measuring the current generated by the redox reaction on the electrode surface.

In recent years, as the need to reduce the sampling volume has increased, one technology trend is to reduce the size of the electrodes of the biochemical test chip to reduce the amount of specimen required. However, the reduction in the size of the electrode results in low or weak electrochemical signals. Therefore, biochemical test chips are often additionally disposed with a conductive medium to enhance the measurement signal. However, adding the conductive medium will increase the manufacturing cost and the difficulty in dissolving and drying. Moreover, when measuring specimens with high concentrations, a bottleneck effect may occur when the flow of electrons reacting to the working electrode exceeds the total amount that can be reacted with the counter electrode, thereby limiting the range of concentrations that can be measured by the biochemical test chip.

The "prior art" discussion above merely provides a technology background without acknowledging that the "prior art" discussed above reveal the subject matter of this disclosure and do not constitute prior art at this time, and that any of the "prior art" discussion above should not be regarded as any part of the present application.

SUMMARY OF THE INVENTION

The present disclosure provides a biochemical test chip, including an insulating substrate, an electrode unit, a first insulating septum, a reactive layer, and a second insulating septum. The electrode unit is located on the insulating substrate. The electrode unit includes a working electrode and a counter electrode, wherein the current density of the counter electrode is greater than the current density of the working electrode. The first insulating septum is located on the electrode unit. The first insulating septum has a first opening, wherein the first opening at least partially exposes the electrode unit. The reactive layer is located on the first opening and is electrically connected to the electrode unit. The second insulating septum is located on the first insulating septum.

In some embodiments, the current density of the counter electrode is greater than or equal to density of the working electrode.

In some embodiments, the area of the counter electrode is smaller than or equal to the area of the working electrode.

In some embodiments, the reactive layer and a target analyte undergo a primary reaction, and the counter electrode is configured to undergo a secondary reaction, wherein the secondary reaction does not interfere with the primary reaction, and the secondary reaction allows the counter electrode to have the capability to receive or release additional electrons.

In some embodiments, the counter electrode includes a first portion and a second portion, wherein the first portion and the reactive layer do not overlap with each other.

In some embodiments, the counter electrode includes a first portion and a second portion, wherein the opening at least partially exposes the first portion.

In some embodiments, the biochemical test chip further includes a protective layer, which is electrically connected to the electrode unit.

In some embodiments, the electrode unit further includes a second counter electrode, wherein the counter electrode and the second counter electrode are separated from each other.

In some embodiments, a standard reduction potential of the counter electrode is greater than a standard reduction potential of the second counter electrode.

In some embodiments, the sum of the area of the counter electrode and the area of the second counter electrode is smaller than or equal to the area of the working electrode.

In some embodiments, the counter electrode is a cathode, and the standard reduction potential of an active material of the counter electrode satisfies $E_s^0 > E_m^0 - E_v$, where the $E_s^0$ is the standard reduction potential of the active material, the $E_m^0$ is the standard reduction potential for the concentration reaction on the working electrode, and the $E_v$ is the potential applied by a measuring apparatus when providing the measuring reaction.

In some embodiments, the counter electrode is an anode, and the standard reduction potential of an active material of the counter electrode satisfies $E_s^0 < E_m^0 - E_v$, wherein the $E_s^0$ is the standard reduction potential of the active material, the $E_m^0$ is the standard reduction potential for the concentration reaction on the working electrode, and the $E_v$ is the potential applied by a measuring apparatus when providing the measuring reaction.

The present disclosure's biochemical test chip has a counter electrode with a current density greater than the current density of the working electrode. Therefore, it is feasible to make the electrons oxidized or reduced by the counter electrode equal to the electrons reduced or oxidized by the working electrode without increasing the area of the counter electrode. In this way, the present biochemical test chip can address the above-mentioned bottleneck effect and meet the current need for reducing the sampling volume.

The foregoing outlines the technical features and advantages of the present disclosure so that those skilled in the art may better understand the following detailed description of the present application. Other technical features and advantages that constitute the subject matter of the present disclosure are described below. Those skilled in the art should appreciate that they may readily use the concepts and specific embodiments provided below as a basis for designing or modifying other structures and processes for carrying out the same purposes and/or achieving the same advantages of the present disclosure. Those skilled in the art should also realize that such equivalent constructions still fall within the spirit and scope of the present disclosure as defined in the appended claims.

BRIEF DESCRIPTION OF THE DRAWINGS

Aspects of the present disclosure are best understood from the following detailed description and claims when read with the accompanying figures. It is noted that, elements with the same reference numbers are the same elements.

FIG. 3A and FIG. 3B are schematic diagrams illustrating the electrochemical reaction according to some embodiments of the present disclosure.

DETAILED DESCRIPTION

Figure 1:
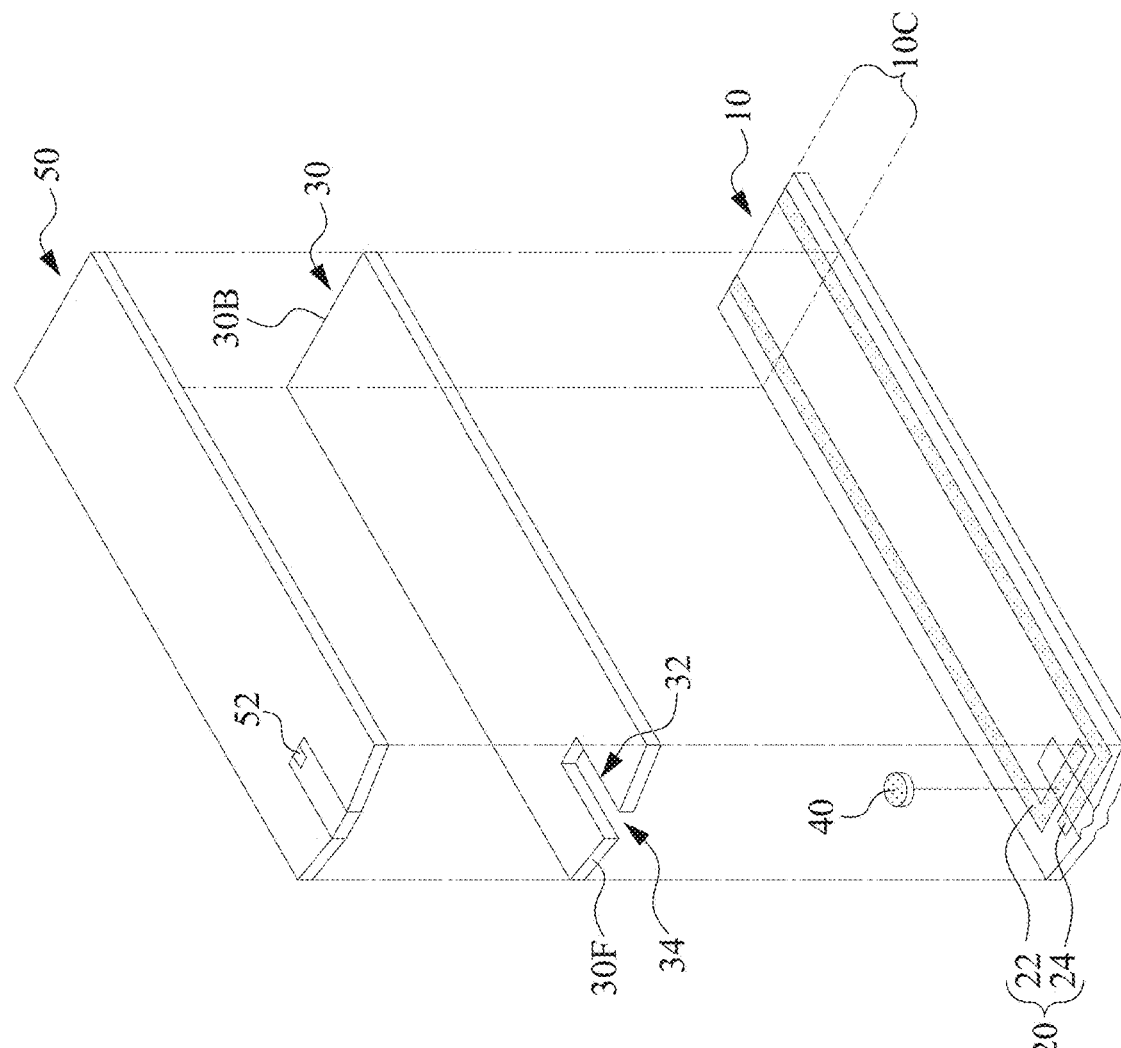
FIG. 1 is a schematic exploded view illustrating a biochemical test chip according to some embodiments of the present disclosure.

Detailed description of the present disclosure is discussed in detail below. However, it should be understood that the embodiments provide many inventive concepts that can be applied in a variety of specific contexts. The specific embodiments discussed are illustrative of the specific ways they can be made and used and do not limit the present disclosure's scope.

The same reference numeral is configured to represent the same elements/components in the various drawings and illustrative embodiments. Reference will now be made in detail to the illustrative embodiments shown in the drawings. Whenever possible, the same reference numeral is used in the drawings and the specification to represent the same or similar parts. In the drawings, the shape and thickness may be exaggerated for clarity and convenience. The description will be directed specifically to the elements forming part of, or more directly cooperating with, the device disclosed hereunder. As could be appreciated, elements not explicitly shown or described may take various forms. The reference to "some embodiments" or "embodiment" throughout this specification implies that the particular features, structures, or characteristics described in conjunction with the embodiment are included in at least one of the embodiments. Therefore, the phrase "in some embodiments" or "in an embodiment" appearing in various places throughout this specification does not necessarily refer to the same embodiment. Besides, the specific features, structures, or characteristics may be combined in any suitable manner in one or more embodiments.

In the drawings, the same reference numeral is configured to indicate the same or similar elements in the various views, and illustrative embodiments of the present application are shown and described. The drawings are not necessarily drawn to scale, and in some cases, the drawings have been exaggerated and/or simplified and are configured for illustrative purposes only. Many possible applications and variations of the present application will be understood by those of ordinary skill in the art in view of the following illustrative embodiments of the present disclosure.

Unless otherwise defined, all terms used herein, including technical and scientific terms, have the same meanings as those commonly understood by a person of ordinary skill in the art in the field of the disclosed embodiments. It should be understood, for example, that terms defined in common dictionaries should be construed to have meanings consistent with their meanings in the relevant field and context of this disclosure and should not be construed or understood to have meanings that are too formal unless expressly defined herein.

Besides, the following embodiments are provided to illustrate the core value of this disclosure but are not intended to limit the scope of protection of this disclosure. For clarity and ease of understanding, the same or similar functions or elements among this disclosure's different embodiments are not repeated or shown in the drawings. Besides, different elements or technical features from different embodiments may be combined or substituted to create further embodiments that are still covered by this disclosure, provided they do not conflict with each other.

The present disclosure is directed to an electrochemical system in which the counter electrode undergoes the self-secondary redox reaction to provide additional electrons; in particular, to a biochemical test chip utilizing the electrochemical system in which the counter electrode undergoes the self-secondary redox reaction. Furthermore, the present disclosure is directed to a counter electrode having an active material, which is capable of providing the same amount of electrons generated by the reaction of the conductive medium on the working electrode by its own secondary redox reaction when the electrode area is limited or when the concentration of the conductive medium on the surface of the counter electrode in the reaction solution is insufficient for electron transfer. As a result, the counter electrode's capability in balancing the electric neutrality can be improved, and the electrochemical circuit can be stabilized to avoid a current bottleneck effect on the counter electrode. In some embodiments, the biochemical test chip further includes a protective layer to help stabilize the active material on the counter electrode, thereby protecting the biochemical test chip and mitigating or avoiding unexpected variations in the biochemical test chip and the environment.

Reference is made to FIG. 1; FIG. 1 is a schematic exploded view illustrating a biochemical test chip 100 according to some embodiments of the present disclosure. The biochemical test chip 100 can be an electrochemical test chip, which is a device that can be electrically connected to. The biochemical test chip 100 is configured to collect a specimen and carry out electrochemical reaction therewith so as to detect a target analyte therein. The specimen includes any liquids or soluble solids having therein one target analyte that can be detected using an electrochemical method. For example, the specimen may include blood, tissue fluid, urine, sweat, tears, and other biological samples; however, the present disclosure is not limited thereto. Moreover, the blood can include the whole blood, plasma, serum, etc.; however, the present disclosure is not limited thereto.

Reference is made to FIG. 1; the biochemical test chip 100 includes an insulating substrate 10, an electrode unit 20, a first insulating septum 30, a reactive layer 40, and a second insulating septum 50. The insulating substrate 10 includes a substrate that is electrically insulated. In some embodiments, the material of the insulating substrate 10 can include polyvinyl chloride (PVC), glass fiber (FR-4), polyethersulfone (PES), bakelite, polyethylene terephthalate (PET), polycarbonate (PC), polypropylene (PP), polyethylene (PE), polystyrene (PS), polyimide (PI), glass plate, ceramic or any combination of the above-mentioned materials; however, the present disclosure is not limited thereto. The material of the insulating substrate 10 can be adjusted depending on the system or actual needs.

The electrode unit 20 of the biochemical test chip 100 is located on the insulating substrate 10. The electrode unit 20 is disposed on the insulating substrate 10 and configured to be subjected to the electrochemical measurement. The electrochemical measurement includes analyzing the specimen's concentration using an electrical reaction, such as potentiometry, conductometry, voltammetry, polarimetry, high-frequency titration, amperometry, Coulombic method, electrolysis and the like. The electrode unit 20 includes a working electrode 22 and a counter electrode 24; however, the present disclosure is not limited thereto. The electrode unit 20 can have other electrodes depending on the requirements of the system. The working electrode 22 is the electrode that allows the target analyte to undergo the electrooxidation reaction or electroreduction reaction on the surface thereof and can be used by the measuring apparatus to determine the concentration. In detail, the electrooxidation reaction or electroreduction reaction is an electrochemical reaction in which the target analyte undergoes an exchange between electrical and chemical energy on the surface of the working electrode 22.

The polarity of the working electrode 22 can be an anode or a cathode, depending on the requirement of the measurement reaction. For example, if the target analyte is oxidized on the working electrode 22, the working electrode 22 is an anode; if the target analyte is reduced on the working electrode 22, the working electrode 22 is a cathode. The counter electrode 24 is an electrode that undergoes the electroreduction reaction or electrooxidation reaction corresponding to the working electrode 22 so that the overall electrochemical system satisfies the principles of charge balance. The potential and polarity of the counter electrode 24 are opposite to the potential and the polarity of the working electrode 22. Before being in contact with the specimen, the working electrode 22 and the counter electrode 24 are insulated from each other. After the working electrode 22 and the counter electrode 24 are in in contact with the specimen, they form an electrical loop with the measuring apparatus. In some embodiments, the working electrode 22 and the counter electrode 24 can include a carbon electrode, silver electrode, platinum electrode, etc.; however, the present disclosure is not limited thereto. The materials of the working electrode 22 and the counter electrode 24 can vary depending on the system's requirement.

The first insulating septum 30 is disposed on the insulating substrate 10 and located on the electrode unit 20. The first insulating septum 30 can have an opening 32, wherein the opening 32 at least partially exposes the electrode unit 20. In some embodiments, the opening 32 is located the front side 30F of the first insulating septum 30 and exposes a portion of the electrode unit 20. The opening 32 is configured to define a reaction zone 34 in the biochemical test chip 100; the reaction zone 34 is configured to accommodate the specimen. The portion of the electrode unit 20 exposed from the opening 32 can undergo the electrochemical reaction with the specimen. The size of shape of the opening 32 can be adjusted according to the desired area of the electrode unit 20 and the desired volume of the specimen. In some embodiments, the back side 30B of the first insulating septum 30 exposes a portion of the electrode unit 20 to form a connecting zone 10C. The electrode unit 20 exposed from the connecting zone 10C can be electrically connected to the measuring apparatus. The measuring apparatus and the biochemical test chip 100 are electrically connected to provide the energy required for the electrochemical measurement and analyze the reaction signal. In some embodiments, the material of the first insulating septum 30 includes a PVC insulation tape, PET insulation tape, heat drying insulation paint or ultraviolet (UV) curable insulation paint; however, the present disclosure is not limited thereto.

Figure 2:
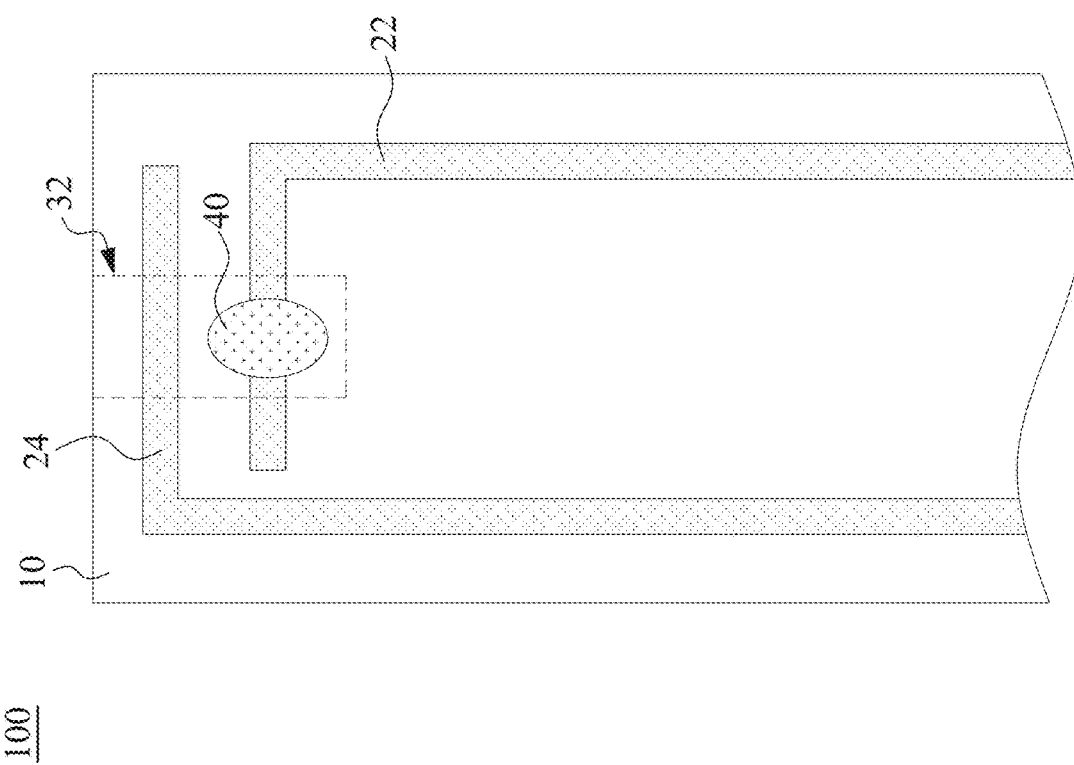
FIG. 2 is a partial top view illustrating a biochemical test chip according to some embodiments of the present disclosure.

FIG. 2 is a partial top view illustrating the biochemical test chip 100 according to some embodiments of the present disclosure. Reference is made to FIG. 2 and FIG. 1 simultaneously; the biochemical test chip 100 further includes a reactive layer 40. The reactive layer 40 is located in the opening 32 of the first insulating septum 30. The reactive layer 40 is located in the reaction zone 34. The reactive layer 40 is configured to undergo a chemical reaction with the specimen. The reactive layer 40 is electrically connected to the electrode unit 20. In some embodiments, the reactive layer 40 is electrically connected to the working electrode 22 of the electrode unit 20. In some embodiments, the area of the reactive layer 40 is smaller than the size of the opening 32. The reactive layer 40 at least partially covers the electrode unit 20 exposed from the opening 32. In the present embodiment, the reactive layer 40 only covers the working electrode 22; however, the present disclosure is not limited thereto. In some embodiments, the reactive layer 40 at least partially contacts the working electrode 22 of the electrode unit 20. In some embodiments, the reactive layer 40 at least partially contacts the working electrode 22 and the counter electrode 24 of the electrode unit 20.

In some embodiments, the reactive layer 40 includes an enzyme and a conductive medium. For example, the enzyme includes a fixed or non-fixed enzyme, such as redox enzymes, antigens, antibodies, microbial cells, animal and plant cells, and biologically identifiable components of animal and plant tissues. The conductive medium is configured to receive electron generated after the reaction between the enzyme and a blood specimen and transmit the electrons to the measuring apparatus via the electrode unit 20. In some embodiments, the conductive medium can include potassium hexacyanoferrate(III), potassium hexacyanoferrate(II) trihydrate, ruthenium complex, ferrocene, sodium dithionite, nicotinamide adenine dinucleotide (NAD+), nicotinamide adenine dinucleotide phosphate (NADP+), thiamin pyrophosphate (TPP), coenzyme A (HSCoA), flavin adenine dinucleotide (FAD) or a combination thereof; however, the present disclosure is not limited thereto. In some embodiments, the reactive layer 40 can be further supplemented with a phosphate buffer and protectants, such as, protein, dextrin, glucan, amino acid, etc.; however, the present disclosure is not limited thereto.

Reference is made again to FIG. 1, the second insulating septum 50 is located on the first insulating septum 30. In some embodiments, the second insulating septum 50 at least partially covers the opening 32 of the first insulating septum 30, so that the opening 32 forms a capillary structure. In some embodiments, the terminus of the second insulating septum 50 is disposed with a vent 502 corresponding to the opening 32. The vent 52 can be of any shapes; for example, the vent 52 can be circular, oval, rectangular, rhombus, etc. The second insulating septum 50 can be of any shapes or sizes. In some embodiments, the second insulating septum 50 also exposes the connecting zone 10C of the electrode unit 20.

Reference is made to FIG. 2 and FIG. 1 simultaneously; the opening 32 of the first insulating septum 30 at least partially exposes the electrode unit 20. The opening 32 at least partially exposes the working electrode 22 and the counter electrode 24. In the present embodiment, at least the working electrode 22 and the counter electrode 24 are disposed in the reaction zone 34; however, the present disclosure is not limited thereto. In other embodiments, electrodes having other functions can be further disposed in the reaction zone 34. Moreover, the present disclosure does not particularly limit the configuration of the electrodes; the working electrode 22 and the counter electrode 24 can be of any shapes. In some embodiments, the working electrode 22 and the counter electrode 24 can have different shapes. In some embodiments, the material of the working electrode 22 is different from or the same as the material of the counter electrode 24.

Figure 3B:
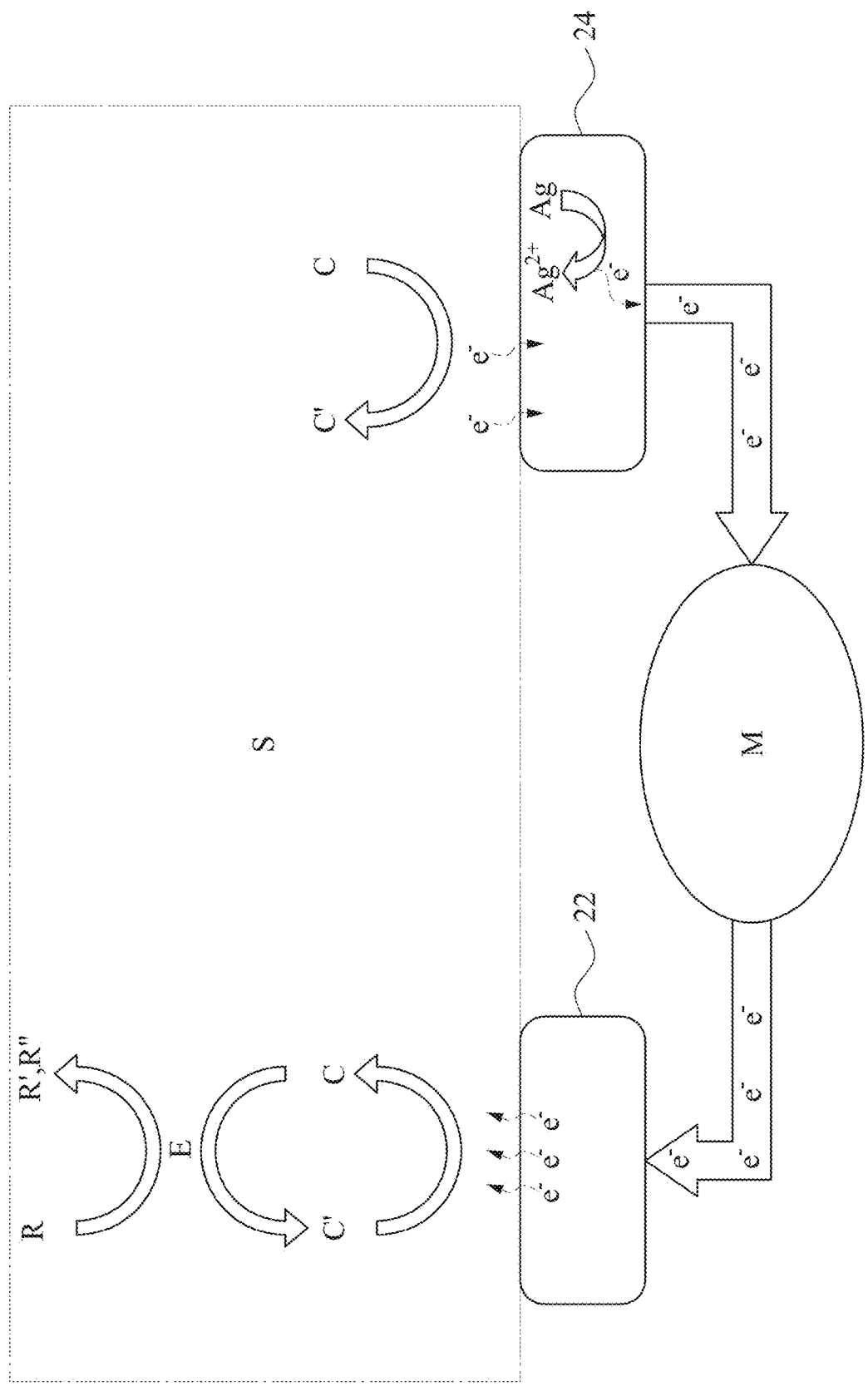

In the present embodiment, the working electrode 22 and the counter electrode 24 are insulated from each other before being in contact with the specimen. When the specimen contacts the working electrode 22 and the counter electrode 24, the working electrode 22 and the counter electrode 24 form an electrical loop with the measuring apparatus. FIG. 3A and FIG. 3B are schematic diagrams illustrating the electrochemical reaction according to some embodiments of the present disclosure. For simplification, FIG. 3A and FIG. 3B only illustrate a portion of the biochemical test chip 100. In detail, FIG. 3A and FIG. 3B only illustrates the portions of the working electrode 22 and the counter electrode 24 within the reaction zone 34. As shown in FIG. 3A and FIG. 3B, the working electrode 22 and the counter electrode 24 exposed from the reaction zone 34 are in in contact with the specimen S and form an electrical loop with the measuring apparatus M. FIG. 3A and FIG. 3B further illustrate the portions of the enzyme E and the conductive medium C within the reaction zone 34, wherein the enzyme E and the conductive medium C form a portion of the reactive layer 40 (shown in FIG. 2). In some embodiments, the conductive medium C can be iron irons; however, the present disclosure is not limited thereto.

Reference is made to FIG. 3A, the specimen S includes a target analyte R, wherein the target analyte R includes an electrochemically active substance or electrochemically reactive substance. After the specimen S is loaded into the reaction zone 34 of the biochemical test chip 100, the target analyte R in the specimen S is reduced by the enzyme E in the reactive layer 40, thereby forming a reduced target analyte R'; however, the present disclosure is not limited thereto. In other embodiments, the target analyte R in the specimen S can be oxidized by the enzyme E in the reactive layer 40, thereby forming an oxidized target analyte R".

The conductive medium C of the reactive layer 40 is configured to receive or provide the electrons generated or lost due to the reaction between the enzyme E and the target analyte R in the specimen S and transmit the electrons to the measuring apparatus M via the working electrode 22 of the electrode unit 20. For simplification, the conductive medium C in this embodiment include, for example, bivalent ferrous irons ($Fe^{2+}$); however, the present disclosure is not limited thereto. When the target analyte R in the specimen S is reduced, the conductive medium C of the reactive layer 40 is oxidized. In the present embodiment, bivalent ferrous irons ($Fe^{2+}$) are oxidized into trivalent ferric irons ($Fe^{3+}$). Moreover, the conductive medium C of the reactive layer 40 is oxidized in an amount corresponding to the amount in which the target analyte R is reduced.

When the conductive medium C of the reactive layer 40 (e.g., $Fe^{2+}$) releases electrons into an oxidized conductive medium C' (e.g., $Fe^{3+}$), the working electrode 22 also undergoes a reaction to reduce the oxidized conductive medium C' (e.g., $Fe^{3+}$) into the reduced conductive medium C (e.g., $Fe^{2+}$). The measuring apparatus M detects the changes in the number of electrons (e) generated by the reaction on the working electrode 22 and carries out the concentration analysis. When the working electrode 22 undergoes the reduction reaction, the counter electrode 24 must oxidize a corresponding amount of the reduced conductive medium C (e.g., $Fe^{2+}$), so that the overall reaction achieves the electrical neutral balance.

Generally, when the oxidizabilty of the counter electrode 24 is insufficient to match the working electrode 22; e.g., the amount of the conductive medium C oxidized by the counter electrode 24 is smaller than the amount of the conductive medium C reduced by the working electrode 22, the level of the reducing current generated by the working electrode 22 is limited due to the principle of electrical neutrality, thereby suffering from the bottle-neck effect. The bottleneck effect caused by the working electrode 22 reacting with more electron flow than the counter electrode 24 can react with will limit the range of the measurable concentration of the biochemical test chip 100.

In the prior art, the occurrence of the aforementioned bottleneck effect is mostly related to the size of the working electrode 22 and the counter electrode 24. The electrochemical oxidation or reduction reaction of the target analyte R in the specimen S generates a certain current change, which is linearly proportional to the concentration of the target analyte R in the specimen S. Therefore, the concentration of the target analyte R in the specimen S can be analyzed by measuring the oxidation or reduction current on the surface of the working electrode 22, and the relationship between current and concentration can be expressed as:

$$i = \frac{nFAC_0\sqrt{D}}{\sqrt{\pi t}},$$

where, I is the measured current (unit: A); n is the number of the electrons generated during the redox reaction; F is the Faraday constant (96500 C/mol); A is the surface area of the working electrode (unit: cm$^2$); $C_0$ is the initial concentration of the specimen (unit: mol/cm$^3$); D is the diffusion constant (unit: cm$^2$/s); t is time (unit: s). in view of the foregoing, the level of the current signal of the electrochemical reaction is proportional to the surface area of the electrode.

In the prior art, in order to save the manufacturing process, the working electrode 22 and the counter electrode 24 are mostly made of the same material. In addition, to avoid additional background signal interference caused by oxidation reduction of the electrode material itself and to consider the lifetime of the electrode, the material of the working electrode 22 and the counter electrode 24 are mostly made of inert carbon. In other embodiments, the materials of the working electrodes 22 and counter electrodes 24 include gold, palladium, etc. In other prior art embodiments, the material of the working electrode 22 is mostly selected from materials that are more reactive with the target analyte R of the specimen S compared to the material of the counter electrode 24. The material of the working electrode 22 is often selected to have a better electrochemical activity or electrochemical reactivity than the material of the counter electrode 24. For example, the material of the working electrode 22 is mostly a silver electrode or silver oxide electrode that has better reactivity with the target analyte R, while the material of the counter electrode 24 is mostly a carbon electrode or platinum electrode that has low reactivity with the target analyte R.

Reference is made to FIG. 3B, in the present disclosure, the material of the working electrode 22 and the counter electrode 24 is chosen so that the current density of the counter electrode 24 is greater than the current density of the working electrode 22. In some embodiments, the material of the counter electrode 24 has better electrochemical reactivity compared to that of the working electrode 22. In detail, the material of the counter electrode 24 is selected to have a better electrochemical reactivity with environmental substances. Said environmental substances refer to substances that are not the target analyte R of the specimen S. In some embodiments, the material of the counter electrode 24 has a better electrochemical activity than the material of the working electrode 22. The material of the counter electrode 24 is selected to have a better electrochemical reactivity with the material of the environmental substance. In some embodiments, the area of the counter electrode 24 may be smaller than or equal to the area of the working electrode 22. In some embodiments, the current density of the counter electrode 24 is greater than or equal to two times the current density of the working electrode 22.

In the present embodiment, the counter electrode 24 can include a conductive active material. In some embodiments, the active material may be doped in the counter electrode 24. In some embodiments, the active material may be formed on the surface of the counter electrode 24. In some embodiments, the counter electrode 24 is composed of the active material. The purpose of using the active material is that when the biochemical test chip 100 undergoes an electrochemical reaction, the active material of the counter electrode 24 can carry out its own oxidation or reduction reaction without interfering with the primary reaction. Said primary reaction refers to the oxidation or reduction reaction caused by the target analyte R and the reaction layer 40, and said secondary reaction refers to the oxidation or reduction reaction that is not caused by the target analyte R and the reaction layer 40. In detail, as long as the secondary reaction occurring on the counter electrode 24 does not affect the primary reaction of the working electrode 22, the source of the reactants is not limited. Therefore, the materials required for the secondary reaction can come from either the specimen S or the environment. The active material of the counter electrode 24 refers to a substance that can undergo redox within the working voltage range. The working voltage refers to the voltage provided by the measuring apparatus M to cause the working electrode 22 and the counter electrode 24 to perform the electrochemical reaction. In some embodiments, the working voltage is ±10 volts (V). In other embodiments, the working voltage is ±5V. In some embodiments, the working voltage is ±2V. In some embodiments, the working voltage is ±1V.

Reference is made to FIG. 3B. Since the counter electrode 24 of the present embodiment includes a conductive active material, it can and undergo the secondary reaction without interfering the primary reaction. Said secondary reaction allows the counter electrode 24 to have the ability to receive or release additional electrons. Said additional electrons refer to electrons not generated by the enzyme E or the conductive medium C of the reactive layer 40. In other words, in addition to undergo the electrochemical reaction with the target analyte R in the specimen S, the counter electrode 24 can obtain electrons by undergoing the secondary reaction with the active material without disrupting the electrical neutrality of the measuring apparatus M.

As shown in FIG. 3B, after the specimen S is filled in the reaction zone 34 and the measuring apparatus M supplies the working voltage, the target analyte R in the specimen S and the enzyme E of the reactive layer 40 undergo the reaction, and a corresponding amount of the oxidized conductive medium C' on the working electrode 22 is reduced into the reduced conductive medium C. On the other hand, the counter electrode 24 needs to oxidize the reduced conductive medium C to the oxidized conductive medium C' in an amount that is corresponding to the number of reduced electrons of the working electrode 22 to maintain the electrical neutrality of the overall system. Since the counter electrode 24 of the present disclosure has an active material that can undergo the secondary reaction, when the counter electrode 24 oxidizes the reduced conductive medium C and receives electrons, it also performs an oxidation reaction at the same time to generate additional electrons. In this embodiment, the materials of the working electrode 22 and the counter electrode 24 are selected so that the current density of the counter electrode 24 is greater than the current density of the working electrode 22. The active material of the counter electrode 24 can perform its own oxidation or reduction reaction without interfering with the primary reaction.

Reference is made again to FIG. 1 and FIG. 2, the working electrode 22 is an electrode for analyzing electro-oxidation or electro-reduction current. Therefore, the working electrode 22 is composed of an inactive material that does not cause interference on the electrode surface. It is worth noting that the inactive material referred to in the present disclosure means that the material will not undergo oxidation or reduction reactions in the measurement environment of the biochemical test chip 100. In other words, the inactive material referred to in this disclosure may have redox capability in other specific environments, but the inactive material will not undergo redox reaction during the measurement process according to the present disclosure. The inactive material of the working electrode 22 may include a conductive material. For example, the inactive material of the working electrode 22 may include palladium, platinum, gold, carbon or a combination thereof, but the disclosure is not limited thereto. The inactive material of the working electrode 22 can be adjusted depending on system requirements.

On the other hand, the active material of the counter electrode 24 refers to the material that undergoes oxidation or reduction in the measurement environment of the biochemical test chip 100. The redox change of the active material of the counter electrode 24 has a direct or indirect causal relationship with the measurement environment of the biochemical test chip 100. In the present disclosure, the characteristics of the material of the counter electrode 24 must match the characteristics of the working electrode 22. For example, if the working electrode 22 performs an electro-reduction reaction, the active material of the counter electrode 24 must be a material with its own oxidizing ability. In other embodiments, if the surface of the working electrode 22 undergoes an electro-oxidation reaction, the counter electrode 24 must be a material with its own reducing ability.

It is worth noting that, in order to ensure that the active material of the counter electrode 24 can perform the preset function during the electrochemical measurement, excessive reaction before the measurement should be avoided; so, the active material of the counter electrode 24 of the present disclosure is in contact with the reaction layer 40 to prevent the two from reacting with each other before measurement. To prevent the two from reacting before the measurement. However, during the electrochemical measurement of the biochemical test chip 100, the reaction layer 40 also needs to react with the counter electrode 24, so the smaller the distance between the working electrode 22 and the counter electrode 24, the better. In some embodiments, the active material of the counter electrode 24 may be covered with a protective film, wherein the protective film may melt after the specimen S enters.

In some embodiments, the active material of the counter electrode 24 can include, but is not limited to, silver (Ag), tin (Sn), iron (Fe), zinc (Zn), cobalt (Co), nickel (Ni), lead (Pb), copper (Cu), manganese dioxide ($MnO_2$), ferroferric oxide ($Fe_3O_4$), ferric oxide ($Fe_2O_3$), ferrous oxide (FeO), silver chloride (AgCl), cobalt trioxide ($Co_2O_3$), cobalt (II) oxide (CoO), nickle (III) oxide ($Ni_2O_3$), nickle (II) oxide (NiO), copper oxide (CuO), cuprous oxide ($Cu_2O$), benzoquinone, ferrocene, ferrocenium, spinel structure mix-valence metal oxides (e.g., $Fe_3O_4$, $Co_3O_4$, etc.), ferrocyanide, Prussian blue ($Fe_4[Fe(CN)_6]_3$), metal ferricyanides ($[Fe(CN)_6]^{3-}$), metal ferrocyanides ($[Fe(CN)_6]^{4-}$), metal complexes, or a combination thereof; however, the present disclosure is not limited thereto.

Reference is made again to FIG. 3B; for simplification, silver (Ag) is used as an example of the active material of the counter electrode 24; however, the present disclosure is not limited thereto. In detail, since silver (Ag) in the counter electrode 24 is in direct contact with the specimen S, in addition to the working voltage applied by the measuring apparatus M, the reaction zone 34 further comprises water ($H_2O$) or hydroxide ions ($OH^-$) that allow silver (Ag) to be oxidized. Therefore, under appropriate conditions, silver in the counter electrode 24 can undergo oxidation reaction with the hydroxide ions ($OH^-$), water ($H_2O$) or water vapor from the specimen S or the environment, and the reaction formula can be expressed as $2Ag+2OH^- \rightarrow Ag_2O+H_2O+2e^-$ or $2Ag+H_2O \rightarrow Ag_2O+2H^++2e^-$. Silver oxide ($Ag_2O$), water ($H_2O$) and electrons are generated after the silver and hydroxide ions ($OH^-$) or water from the specimen S or the environment undergo redox reaction. Therefore, with respect to the overall reaction, the counter electrode 22 is also self-oxidized to form the oxidized electrode (silver oxide) and release electrons (e), in addition to oxidize the reduced conductive medium C (e.g., $Fe^{2+}$). Hence, electrons generated by the active material of the counter electrode 24 help to improve the overall electrical neutrality of the counter electrode 24 under the principle of conservation of charge.

Thus, when the working electrode 22 undergoes extensive electroreduction, the counter electrode 24 can undergo electrooxidation correspondingly to satisfy the overall system's electrical neutrality. It should be noted that although the active material (e.g., silver) of the counter electrode 24 consumes water ($H_2O$) or hydroxide ions ($OH^-$) and produces hydrogen ions ($H^+$) or water ($H_2O$) during the oxidation process, and thereby partially changes the pH of the reaction zone 34, the resulted change in pH is minimal for the overall system. Hence, the pH change does not affect the primary reaction and the test results, and can be ignored.

To ensure that the active material of the counter electrode 24 has the above-mentioned capabilities, the active material and the counter electrode 24 must have the same reaction polarity. In other words, although the change in the oxidation number of the active material and the counter electrode 24 may not be equal, when the counter electrode 24 is an anode, the active material must have oxidizing ability; when the counter electrode 24 is a cathode, the active material must have reducing ability. Therefore, the selection of the active material needs to match the reaction polarity of the counter electrode 24, and it must be chosen to improve the electrical neutrality ability of the counter electrode 24 under the principle of conservation of charge. Therefore, when the counter electrode 24 is an anode, the standard reduction potential of the active material of the counter electrode 24 must satisfy $E_s^0 > E_m^0 - E_v$. Here, $E_s^0$ is the standard reduction potential of the active material, $E_m^0$ is the standard reduction potential of the concentration reaction on the working electrode 22; $E_v$ is the potential applied by the measuring apparatus M when providing the measuring reaction.

In some embodiments, the conductive medium C is ferrocyanide ($Fe^{II}(CN)_6^{4-}$), the working voltage ($E_v$) applied by the measuring apparatus M is +0.4V, the working electrode 22 undergoes oxidation reaction, and hence the reaction of the conductive medium C on the surface of the working electrode 22 is $Fe^{II}(CN)_6^{4-} \rightarrow Fe^{III}(CN)_6^{3-}+e^-$, wherein $E_m^0=0.36V$. Therefore, in the present embodiment, the standard reduction potential ($E_s^0$) of the active material of the counter electrode 24 undergoing the reduction reaction must be greater than −0.04V; thus, the material with a standard reduction potential ($E_s^0$) greater than −0.04V can be chosen as the material for the counter electrode 24, such as, $Fe_3O_4$ ($E^0=+0.085V$), AgCl ($E^0=+0.2223V$), ferrocenium ($E^0=+0.4V$), benzoquinone ($E^0=+0.6992V$) and the like; however, the present disclosure is not limited thereto.

In some embodiments, the conductive medium C is ferricyanide ($Fe^{III}(CN)_6^{3-}$), the working voltage ($E_v$) applied by the measuring apparatus M is −0.4V, the working electrode 22 undergoes reduction reaction, and hence the reaction of the conductive medium C on the surface of the working electrode 22 is $Fe^{III}(CN)_6^{3-}+e^- \rightarrow Fe^{II}(CN)_6^{4-}$, wherein $E_m^0=0.36$ V. Therefore, in the present embodiment, the standard reduction potential ($E_s^0$) of the active material of the counter electrode 24 undergoing the reduction reaction must be less than 0.76V; thus, the material with a standard reduction potential ($E_s^0$) smaller than 0.76V can be chosen as the material for the counter electrode 24, such as, ferrocene ($E^0=+0.4V$), Cu ($E^0=+0.34V$), Fe ($E^0=+0.085V$), Sn ($E^0=-0.1V$), and the like; however, the present disclosure is not limited thereto.

The foregoing is only an example of the active material of the counter electrode 24, and the present disclosure is not limited thereto. Moreover, the standard reduction potential of the active material of the counter electrode 24 is not limited to the foregoing. As discussed above, one should consider the polarity of the active material of the counter electrode 24, wherein the polarity of active material should be the same as the polarity of the measuring reaction on the counter electrode 24. Further, the standard reduction potential of the active material of the counter electrode 24 should satisfy the condition of $E_s^0 < E_m^0 - E_v$ or $E_s^0 > E_m^0 - E_v$. In some embodiments, $E_v$ can be ±5 V~±2 mV. In some embodiments, $E_v$ can be ±2 V~±80 mV. In some embodiments, $E_v$ can be ±0.8 V~±0.1 V.

The present disclosure is not limited to the foregoing embodiments, and can comprise other different embodiments. For simplification purposes and to facilitate the comparison among embodiments of the present disclosure, in the following embodiments, each of the completely the same elements is labeled with completely the same reference numeral. To further facilitate the comparison among the differences between these embodiments, only the differences among different embodiments are discussed, whereas the completely the same features are not discussed for the sake of brevity.

Figure 4:
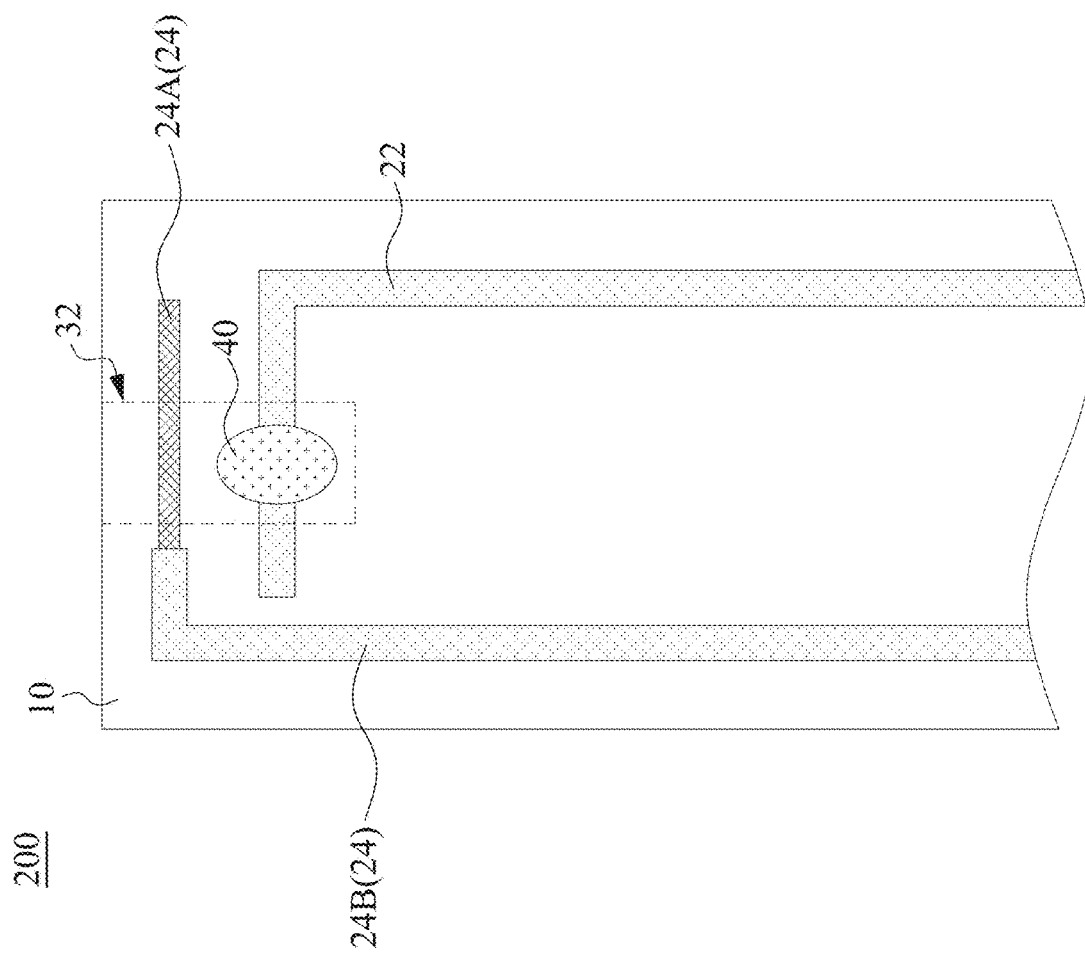
FIG. 4 is a partial top view illustrating a biochemical test chip according to some embodiments of the present disclosure.

FIG. 4 is a partial top view illustrating a biochemical test chip according to some embodiments of the present disclosure. As shown in FIG. 4, the difference between the biochemical test chip 200 and the biochemical test chip 100 is that the counter electrode 24 includes a first portion 24A and a second portion 24B. In some embodiments, the counter electrode 24 can include inactive material and active material. For example, in the present embodiment, the first portion 24A of the counter electrode 24 includes an active material, whereas the second portion 24B includes an inactive material. Therefore, the first portion 24A is capable of receiving or releasing additional electrons.

In some embodiments, the active material can be disposed on the insulating substrate 10 first, and then the inactive material can be applied onto a predetermined position to form the first portion 24A and the second portion 24B of the counter electrode 24 according to the present embodiment. In some embodiments, the inactive material can be disposed on the insulating substrate 10 first, and then the active material are disposed on the predetermined location of the opening 32 to form the first portion 24A and the second portion 24B of the counter electrode 24 according to the present embodiment. In this way, the first portion 24A (active material) of the counter electrode 24 is exposed from the opening 32.

The method for disposing the first portion 24A and the second portion 24B of the counter electrode 24 can include techniques like screen printing, imprinting, thermal transfer printing, spin coating, ink-jet printing, laser ablation, deposition, electrodeposition, etc.; however, the present disclosure is not limited thereto. In some embodiments, monomers with redox capability are polymerized on the inactive material surface of the counter electrode 24 using plasma or other means for chemical bonding modification to form polymers, such as polyaniline, polypyrrole, polythiophene, polyvinylferrocene, etc.; however, the present disclosure is not limited thereto. In some embodiments, the inactive material surface of the counter electrode 24 can be grafted with high molecular chains and bonded with conductive medium with redox capabilities (such as, ferrocenecarboxylic acid, to form the counter electrode 24.

Figure 5:
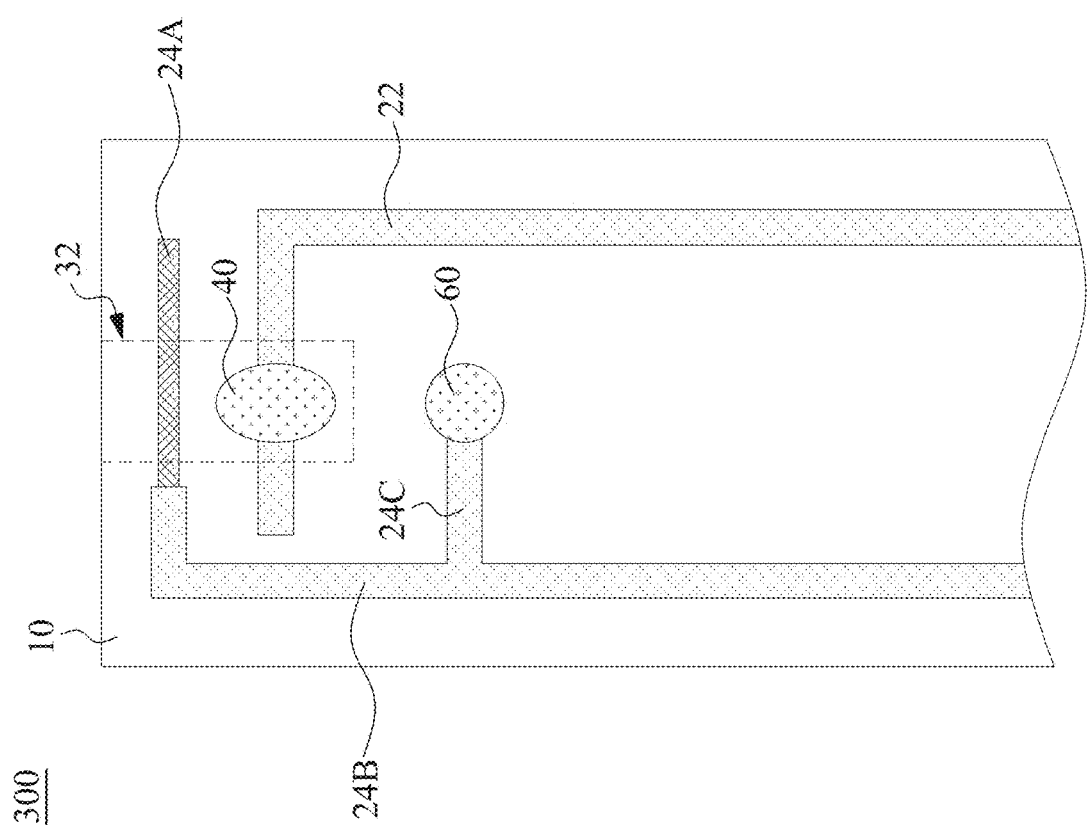
FIG. 5 is a partial top view illustrating a biochemical test chip according to some embodiments of the present disclosure.

FIG. 5 is a partial top view illustrating a biochemical test chip according to some embodiments of the present disclosure. As shown in FIG. 5, the difference between the biochemical test chip 300 and the biochemical test chip 200 is that the biochemical test chip 100 further including the protective layer 60. For example, the counter electrode 24 exposed to the environment may get spoiled upon being oxidized with the water vapor or oxygen in the air. The biochemical test chip 300 includes an additional protective layer 60 to protect the stability of the active material of the counter electrode 24. The protective layer 60 can be configured to protect the counter electrode 24 in the biochemical test chip 300 to slow the unexpected spoilage of the first portion 24A of the counter electrode 24 in the environment, wherein said spoilage may result in no or reduced receipt or release of additional electrons.

The protective layer 60 is disposed on specific regions in the electrode unit 20. In some embodiments, the protective layer 60 electrically connected to the first portion 24A of the counter electrode 24 via the electrode unit 20. For example, in the present embodiment, the protective layer 60 is electrically connected to the first portion 24A and the second portion 24B of the counter electrode 24 via the branch 24C of the counter electrode 24. In some embodiments, the counter electrode 24 do not have the branch 24C, and the protective layer 60 can be disposed directly on the second portion 24B of the counter electrode 24 so that it is electrically connected to the first portion 24A of the counter electrode 24. In some embodiments, the protective layer 60 and the first portion 24A of the counter electrode 24 locate on the same level. In some embodiments, the protective layer 60 and the first portion 24A of the counter electrode 24 locate on different levels. For example, the protective layer 60 can be disposed above or under the counter electrode 24. In some embodiments, the protective layer 60 can be surrounded by the second portion 24B of the counter electrode 24.

In some embodiments, the first insulating septum 30 can have a first opening (not shown in the drawings), and the second insulating septum 50 can have a second opening (not shown in the drawings), wherein the first opening and second opening at least partially expose the protective layer 60. The protective layer 60 and the counter electrode 24 can be exposed to the same environment; however, the present disclosure is not limited thereto. For example, the protective layer 60 can be disposed between the insulating substrate 10 and the first insulating septum 30, and is exposed to same environment as the first portion 24A of the counter electrode 24 via the first opening and the second opening. In other embodiments, the protective layer 60 and the counter electrode 24 can be exposed to different environment. For example, the protective layer 60 can be disposed between the insulating substrate 10 and the first insulating septum 30, and the first insulating septum 30 and the second insulating septum 50 do not have the first opening and the second opening. The position of the protective layer 60 is not limited to those described the above, in some embodiments, the protective layer 60 can be disposed on the second insulating septum 50 and electrically connected to the electrode unit 20 via wires. In other embodiments, the protective layer 60 can be disposed between the first insulating septum 30 and the second insulating septum 50 and electrically connected to the electrode unit 20 via wires.

The protective layer 60 can take the forms of solid, liquid, or gas. For example, solids can include pure metals, alloys, metal compounds (halides, oxidates, mixed-valence compounds, organometallic complexes), organic redox agents, etc. Liquids can include aqueous solutions, organic solutions, supercritical fluids, liquid elements (e.g., bromine, mercury), etc. Gases can include gaseous elements (e.g., oxygen, ozone), gaseous compounds (e.g., ammonium, nitrogen monoxides) etc.

The protective layer 60 and the counter electrode 24 (or the first portion 24A of the counter electrode 24) may have different materials or compositions. There can be a potential difference ($E_{cell}^0$) between the protective layer 60 and the counter electrode 24. In some embodiments, there is a potential difference ($E_{cell}^0$) between the protective layer 60 and the first portion 24A of the counter electrode 24. The potential difference ($E_{cell}^0$) can be expressed as $E_{cell}^0=E_{cathode}-E_{anode}$, where $E_{cathode}$ is the standard reduction potential of the cathode (the cathode electrode), and $E_{anode}$ is the standard reduction potential of the anode (the anode electrode). The protective layer 60 and the counter electrode 24 (or the first portion 24A of the counter electrode 24) can have different standard reduction potentials.

In the present disclosure, the potential difference ($E_{cell}^0$) between the protective layer 60 and the counter electrode 24 is greater than 0. According to the Gibbs Free Energy relationship, i.e., $\Delta G^0=-nFE_{cell}^0$, where $\Delta G^0$ is the change in the free energy, n is the mole number of electrons, and F is the charge per mole. When the Gibbs free energy $\Delta G^0<0$, the reaction is a spontaneous reaction. From the above, it can be seen that when two oxidizable/reduceable substances with a potential difference ($E_{cell}^0$) are in the same reaction tank, the one with higher standard reduction potential will tend to undergo reduction reaction and the other one will tend to undergo oxidation reaction. For example, when the standard reduction potential of the anode is smaller than that of the cathode, the anode will spontaneously transfer electrons to the cathode, and the cathode will remain in the reduced state because it continues to receive electrons, thus avoiding the influence of environmental oxidants (e.g., oxygen, water vapor, etc.).

The protective layer 60 and the counter electrode 24 are in the same reaction tank. In some embodiments, the protective layer 60 and the counter electrode 24 are in contact with the air at the same time; however, the present disclosure is not limited thereto. The protective layer 60 is electrically connected to the counter electrode 24 and hence it is also considered to be in the same reaction tank. Since there is the potential difference ($E_{cell}^0$) between the protective layer 60 and the counter electrode 24, and the potential difference ($E_{cell}^0$) is greater than 0, an electron flow in a specific direction is generated spontaneously, thereby allowing the subject to be protected (the counter electrode 24 or the first portion 24A of the counter electrode 24) to be kept in the original oxidated/reduced status. In this way, one can protect the biochemical test chip 300 to delay the unexpected spoilage due to the reaction between the biochemical test chip 300 and environment.

In some embodiments, the area of the protective layer 60 is greater than the area of the counter electrode 24 (or the first portion 24A of the counter electrode 24). In some embodiments, the area of the protective layer 60 substantially equals to the area of the counter electrode 24 (or the first portion 24A of the counter electrode 24). The area and thickness of the protective layer 60 and the counter electrode 24 (or the first portion 24A of the counter electrode 24) can be adjusted depending on the system requirements. Depending on the materials of the protective layer 60 and the counter electrode 24 (or the first portion 24A of the counter electrode 24), the protective layer 60 and the counter electrode 24 (or the first portion 24A of the counter electrode 24) can, respectively, be the anode and the cathode, and the protective layer 60 and the counter electrode 24 (or the first portion 24A of the counter electrode 24) can also be the cathode and the anode, respectively.

For simplification, as an example, the material of the first portion 24A of the counter electrode 24 is silver (Ag); however, the present disclosure is not limited thereto. In the present embodiment, the first portion 24A of the counter electrode 24 includes silver. However, silver, when exposed to the air, tends to react with oxygen and water vapor and becomes silver oxide, wherein the oxidation equation can be expressed as $4Ag+O_2 \rightarrow 2Ag_2O$, wherein the standard reduction potential of silver/silver oxide is 1.17 V. When silver is oxidized into silver oxide after being exposed to the air, it will result in the toxification on the surface of the first portion 24A of the counter electrode 24. In this case, the capability of the first portion 24A to receive or release additional electrons will be decreased, and therefore, the bottleneck effect between the working electrode 22 and the counter electrode 24 cannot be improved effectively.

As shown in FIG. 5, the biochemical test chip 300 is disposed with the protective layer 60, and the protective layer 60 is electrically connected to the counter electrode 24. In some embodiments, the protective layer 60 is configured to protect the first portion 24A of the counter electrode 24. In some embodiments, the protective layer 60 can include stannous oxide (SnO). Stannous oxide, when being exposed to the air, tends to undergo oxidation reaction with water vapor, wherein the reaction equation can be expressed as $SnO+H_2O \rightarrow SnO_2+2H^++2e^-$. The standard reduction potential of silver oxide/silver is 1.17 V, whereas the standard reduction potential of stannous oxide/tin oxide −0.09 V. Hence, in the present embodiment, the first portion 24A of the counter electrode 24 is the cathode, and the protective layer 60 is the anode. When the biochemical test chip 300 is exposed to environment with water vapor, the potential difference ($E_{cell}^0$) is 1.08 V. Because the potential difference ($E_{cell}^0$) between the two is greater than 0, the change in the free energy is smaller than 0, and hence, the following reaction will vary out spontaneously: $Ag_2O+SnO \rightarrow 2Ag+SnO_2$. In this case, the half-reaction taking place on the first portion 24A of the counter electrode 24 is $Ag_2O+2H^++2e^- \rightarrow 2Ag+H_2O$.

Therefore, silver oxide in the first portion 24A of the counter electrode 24 is reduced into silver as a result of the oxidation reaction of the stannous oxide in the protective layer 60. When the protective layer 60 undergoes oxidation reaction, the first portion 24A of the counter electrode 24 undergoes the reduction reaction, thereby slowing the oxidation reaction caused by oxygen and water vapor in the air. Further, through the oxidation reaction between the water vapor in the air and stannous oxide, the first portion 24A of the counter electrode 24 is further protected, so as to keep the first portion 24A of the counter electrode 24 stable. Therefore, by disposing the protective layer 60 in the biochemical test chip 300, one can prevent the first portion 24A of the counter electrode 24 from being spoiled before performing the specimen measurement. The compositions and materials of the first portion 24A of the counter electrode 24 and the protective layer 60 are not limited to those described above. In some embodiments, the compositions and materials of the first portion 24A of the counter electrode 24 and the protective layer 60 are chosen so that the potential difference ($E_{cell}^0$) between the two is greater than 0.

The present embodiment provides a biochemical test chip 300 with a protective layer 60, wherein the protective layer 60 can maintain the stability of the active material in the counter electrode 24, so as to protect the biochemical test chip 300 and slow the unexpected spoilage of the biochemical test chip 300 as a result of the reaction with environment before the biochemical test chip 300 is used in specimen measurement, thereby maintain or protecting the capability of the counter electrode 24 of the biochemical test chip 300 in receiving or releasing additional electrons.

Figure 6:
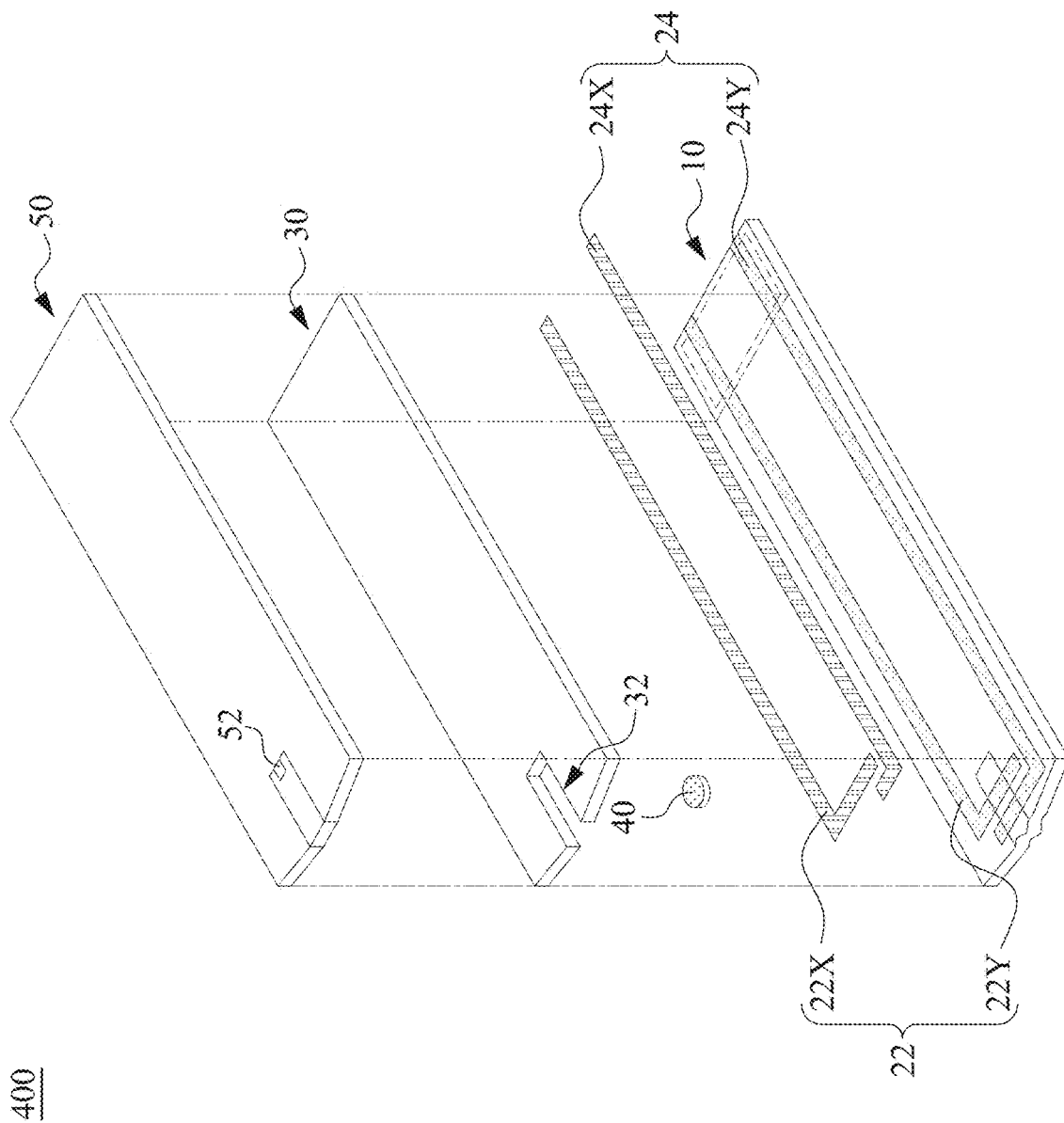
FIG. 6 is a partial top view illustrating a biochemical test chip according to some embodiments of the present disclosure

FIG. 6 is a partial top view illustrating a biochemical test chip according to some embodiments of the present disclosure. As shown in FIG. 6, the difference between the biochemical test chip 400 and the biochemical test chip 100 is that the working electrode 22 and the counter electrode 24 are compound electrode. The working electrode 22 includes a first portion 22X and a second portion 22Y. The counter electrode 24 includes a first portion 24X and a second portion 24Y. In some embodiments, the working electrode 22 and the counter electrode 24 are both made of an inactive material and an active material. For example, in the present embodiment, the first portion 22X of the working electrode 22 and the first portion 24X of the counter electrode 24 include an inactive material, whereas the second portion 22Y of the working electrode 22 and the second portion 24Y of the counter electrode 24 include an active material.

In some embodiments, the inactive material can include carbon, and the active material can include silver. The working electrode 22 and the counter electrode 24 are composed of an inactive material and an active material to increase the overall electrical conductivity and conductivity. The first portion 22X of the working electrode 22 completely overlaps with the second portion 22Y of the working electrode 22, whereas the first portion 24X of the counter electrode 24 does not overlap entirely with the second portion 24Y of the counter electrode 24. In the present embodiment, the first portion 24X of the counter electrode 24 at least partially exposes the second portion 24Y of the counter electrode 24.

In some embodiments, the opening 32 at least partially exposes the second portion 24Y of the counter electrode 24, whereas the opening 32 does not expose the second portion 22Y of the working electrode 22. Since the second portion 24Y of the counter electrode 24 includes an active material, it has the capability to receive or release additional electrons. The second portion 24Y of the counter electrode 24 can receive or release additional electrons from the biochemical test chip 400 during the measurement reaction by being exposed through the opening 32. In this way, the counter electrode 24's capability in maintaining the electrical neutrality can be improved.

In some embodiments, the working electrode 22 and the counter electrode 24 of the present embodiment can be formed by first disposing an active material on the insulating substrate 10 and then covering an inactive material on a predetermined position. The techniques for forming the working electrode 22 and the counter electrode 24 can include screen printing, imprinting, thermal transfer printing, spin coating, ink-jet printing, laser ablation, deposition, electrodeposition, etc.; however, the present disclosure is not limited thereto.

Figure 7:
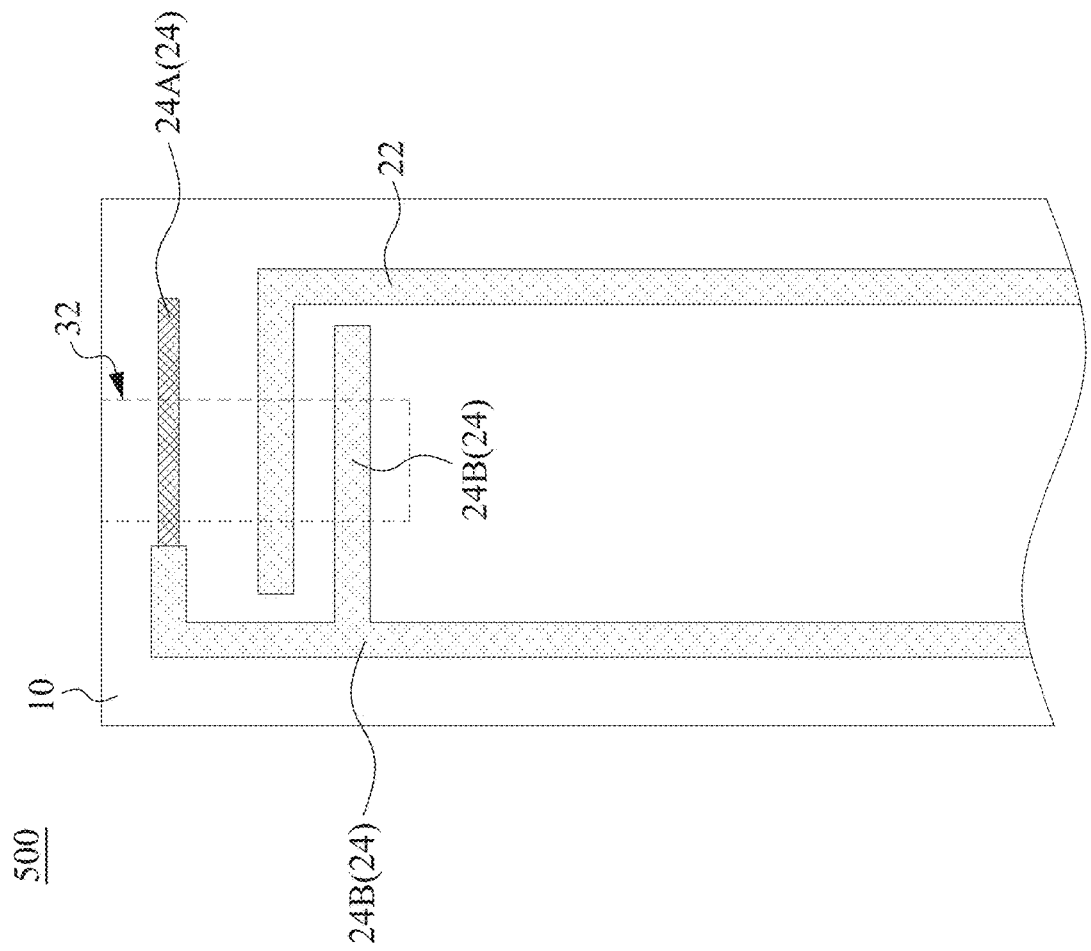
FIG. 7 is a schematic exploded view illustrating a biochemical test chip according to some embodiments of the present disclosure.

FIG. 7 is a schematic exploded view illustrating a biochemical test chip according to some embodiments of the present disclosure. As shown in FIG. 7, the difference between the biochemical test chip 500 and the biochemical test chip 200 is that the counter electrode 24 is in a fork-shape. The counter electrode 24 includes a first portion 24A and a second portion 24B. In some embodiments, the first portion 24A and the second portion 24B are respectively made of an active material and an inactive material. The opening 32 at least partially exposes the first portion 24A and the second portion 24B. In the opening 32, the counter electrode 24 comprises both the active material (the first portion 24A) and the inactive material (the second portion 24B). In the present embodiment, the second portion 24B of the counter electrode 24 is responsible for the conventional task between the counter electrode 24 and the matching working electrode 22, whereas the first portion 24A of the counter electrode 24 utilize its self-oxidation or self-reduction to compensate for the insufficiency in the second portion 24B. In detail, the first portion 24A of the counter electrode 24 can receive or release additional electrons from the biochemical test chip 500 during measurement reaction.

Figure 8:
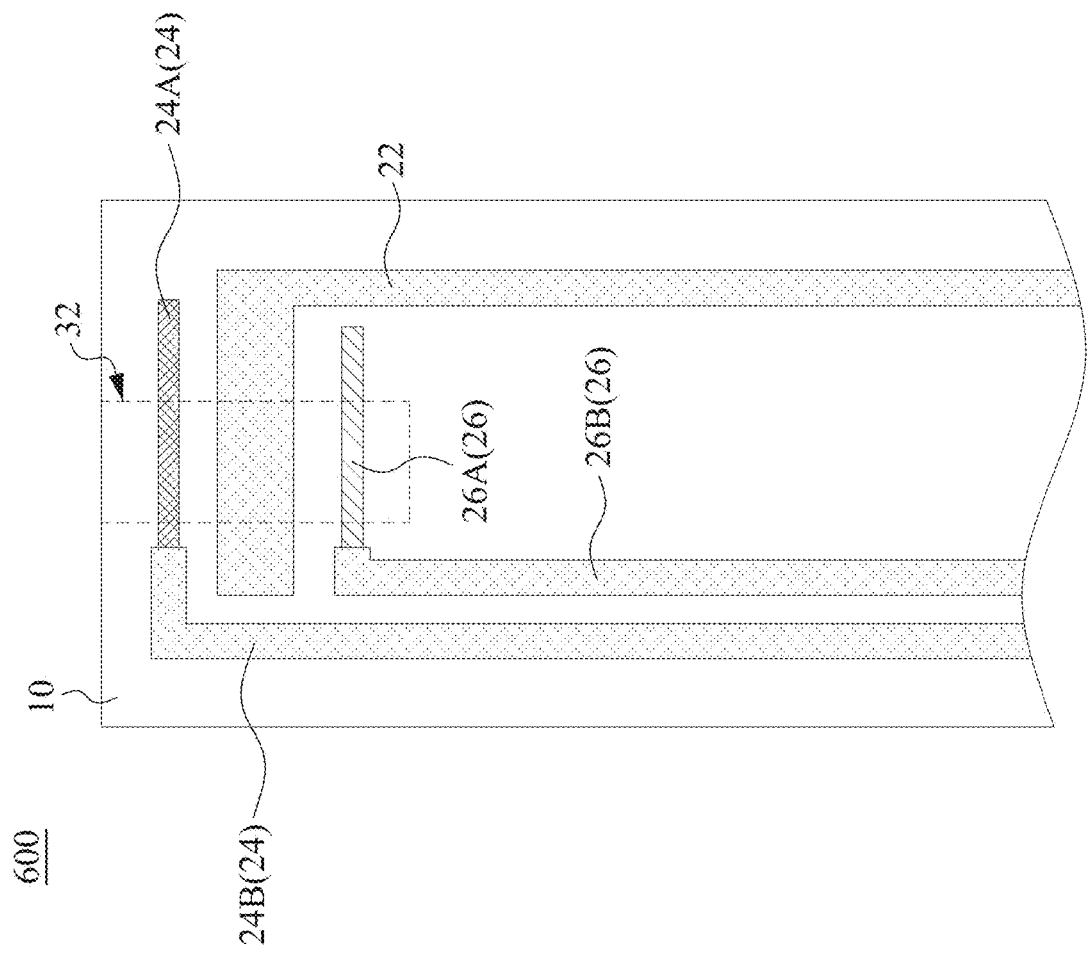
FIG. 8 is a partial top view illustrating a biochemical test chip according to some embodiments of the present disclosure.

FIG. 8 is a partial top view illustrating a biochemical test chip according to some embodiments of the present disclosure. As shown in FIG. 8, the difference between the biochemical test chip 600 and the biochemical test chip 200 is that the biochemical test chip 600 is disposed with a first counter electrode 24 and a second counter electrode 26, wherein the first counter electrode 24 and the second counter electrode 26 are separated from each other. The first counter electrode 24 and the second counter electrode 26 respectively include a first portion 24A, 26A and a second portion 24B, 26B. The first portion 24A of the first counter electrode 24 and the first portion 26A of the second counter electrode 26 include an active material, whereas the second portion 24B of the first counter electrode 24 and the second portion 26B of the second counter electrode 26 include an inactive material. The opening 32 at least partially exposes the first portion 24A of the first counter electrode 24 and the first portion 26A of the second counter electrode 26.

In some embodiments, the material of the first portion 24A of the first counter electrode 24 can undergo self-oxidation reaction, and the material of the first portion 26A of the second counter electrode 26 can undergo self-reduction reaction. In some embodiments, the standard reduction potential of the first counter electrode 24 is greater than the standard reduction potential of the second counter electrode 26. In some embodiments, the standard reduction potential of the first portion 24A of the first counter electrode 24 is greater than the standard reduction potential of the first portion 26A of the second counter electrode 26.

In some embodiments, the area of the first portion 24A of the first counter electrode 24 and the area of the first portion 26A of the second counter electrode 26 are is smaller than or equal to the area of the working electrode 22. In some embodiments, the sum of the areas of the first portion 24A of the first counter electrode 24 and the first portion 26A of the second counter electrode 26 that are exposed in the opening 32 is smaller than or equal to the area of the working electrode 22 that is exposed in the opening 32.

The first portion 24A of the first counter electrode 24 and the first portion 26A of the second counter electrode 26 are configured to receive or release additional electrons from the biochemical test chip 600 during measurement reaction by being exposed in the opening 32. By switching the electrical properties of the first counter electrode 24 and the second counter electrode 26, no bottleneck effect occurs in either the oxidation or reduction reactions of the working electrodes 22. In this way, the biochemical chip 600 can measure the concentration of substances under different reactions.

Figure 9A:
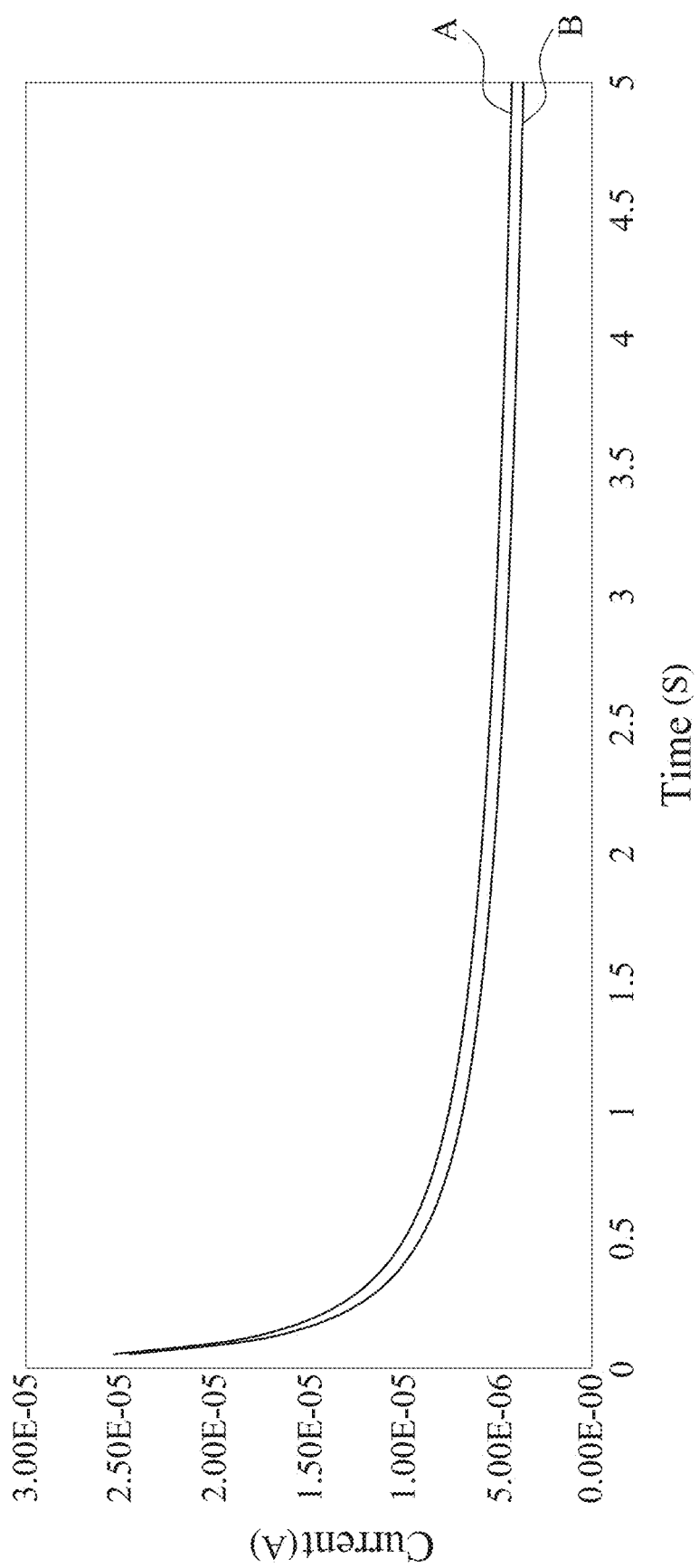
FIGS. 9A and 9B are charts respectively showing the signals detected on a counter electrode according to the present embodiment and a counter electrode of a comparative example under different concentrations.
Figure 9B:
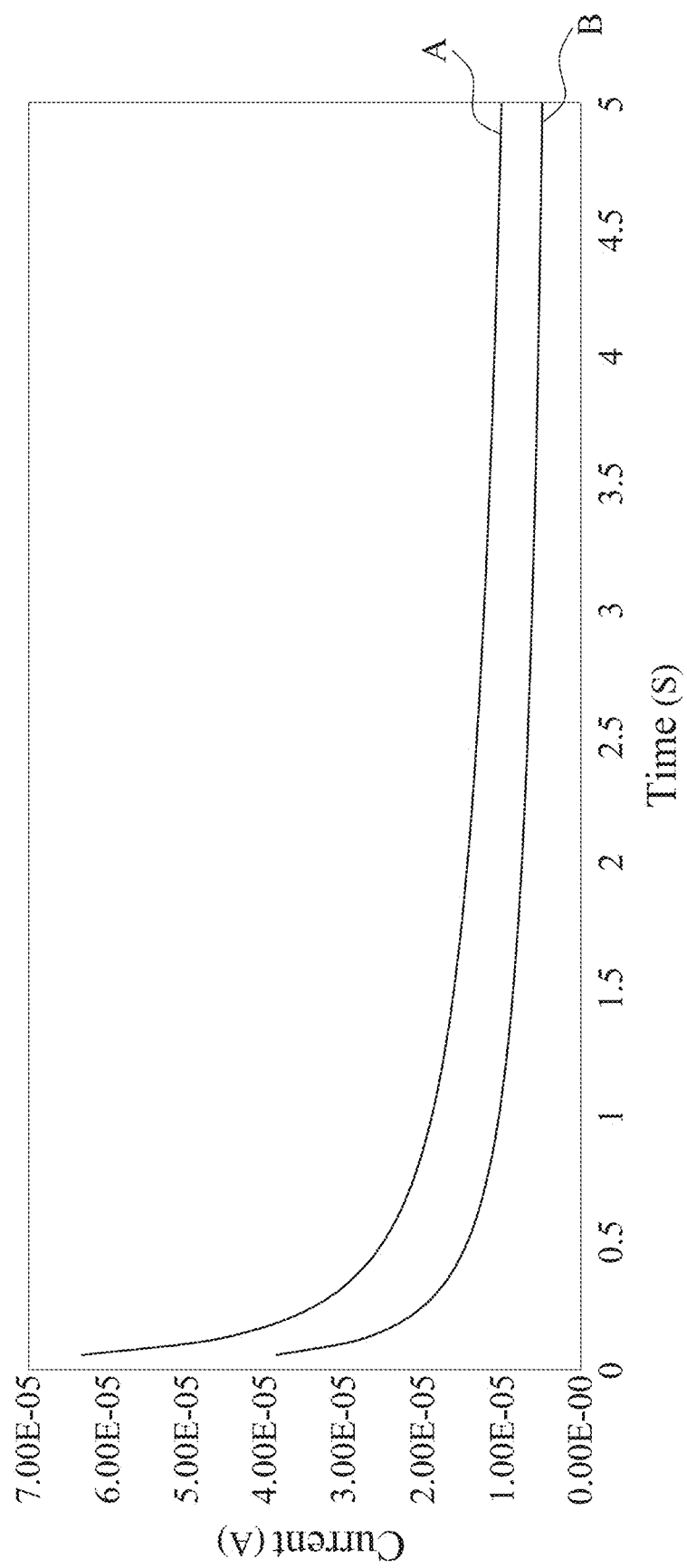

FIGS. 9A and 9B are charts respectively showing the signals detected on a counter electrode according to the present embodiment and a counter electrode of a comparative example under different concentrations, wherein FIG. 9A shows the blood specimen signal of 43% hematocrit 200 mg/dL blood glucose, and FIG. 9B shows the blood specimen signal of 43% hematocrit 600 mg/dL blood glucose. In detail, curve A of FIG. 9A and FIG. 9B shows the blood sample signal of a 4.8 mm²-working electrode with a 0.8 mm²-counter electrode of the disclosed embodiment. Curve B is the blood sample signal of the 4.8 mm²-working electrode with the 2.4 mm²-counter electrode of the comparative example. The working electrode is a carbon electrode. The 0.8 mm²-counter electrode of the embodiments of the present disclosure is a silver oxide electrode; however, the present disclosure is not limited thereto. The 2.4 mm²-counter electrode of the comparative example is a commercially available 2.4 mm²-carbon electrode. Curve A and B show the comparison of the signals using the oxidation concentration measurement method under the same environmental conditions.

As shown in FIG. 9A, since the general counter electrode (inactive material) is sufficient to support the amount of charge transfer for the reduction reaction on the working electrode in a low concentration environment, the signal and performance of the counter electrode of the present embodiment and the counter electrode of the comparative example are almost the same, except for the difference in impedance obtained between Curve A and Curve B.

As shown in FIG. 9B, in a high concentration environment, a bottleneck effect occurs because the general counter electrode (inactive material) cannot match the charge transfer amount of the working electrode at high concentration when the reduction reaction occurs. On the other hand, since the counter electrode of the present embodiment is capable of self-oxidation and self-reduction, it can receive or release additional electrons, so the counter electrode of the present embodiment can measure higher signals using the same area or smaller area compared to a conventional electrode.

Figure 10:
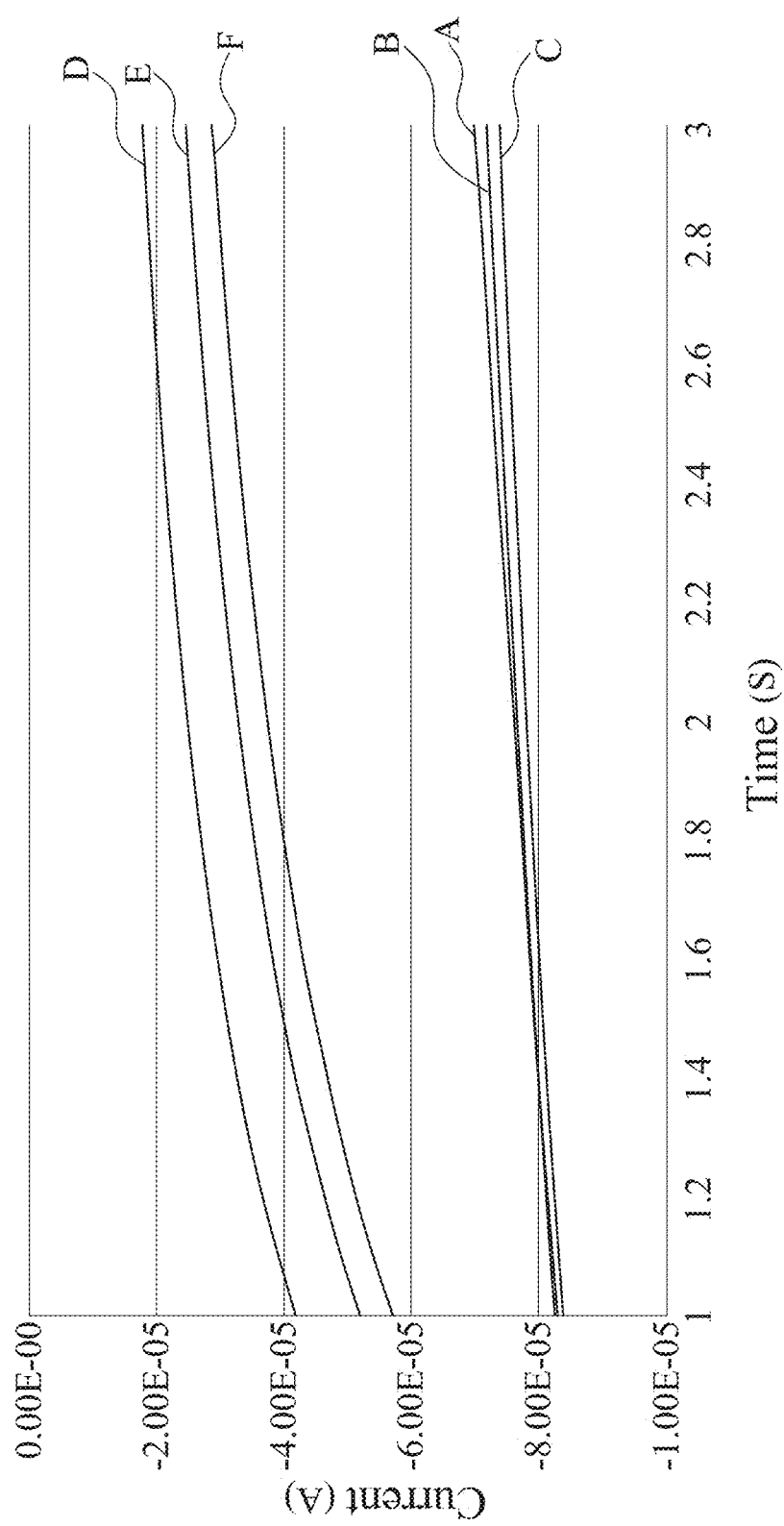
FIG. 10 is a chart showing the signals detected on a counter electrode according to the present embodiment and a counter electrode of a comparative example having different electrode areas.

FIG. 10 is a chart showing the signals detected on a counter electrode according to the present embodiment and a counter electrode of a comparative example having different electrode areas. FIG. 10 shows a comparison of the signals of the reduction concentration measurement method for the high concentration test using the counter electrode of the present embodiment and the counter electrode of the comparative example for a 600 mg/dL blood glucose plasma sample. The working electrode is a carbon electrode with an electrode area of 4.8 mm², and the counter electrode of the present embodiment is a silver electrode with an electrode area of 0.8 mm² (curve A), 1 mm² (curve B), and 1.2 mm² (curve C). The counter electrodes of the comparative example are carbon electrodes with electrode areas of 1.2 mm² (curve D), 1.8 mm² (curve E), and 2.4 mm² (curve F), respectively.

As shown in FIG. 10, the intensity of the response current of the comparative example increases as the area of the counter electrode increases, which means that the area of the counter electrode of the comparative example is still insufficient to support the electron flow through the working electrode and thus creates a bottleneck effect. However, in the present embodiment, the current density of counter electrode area does not increase as the area of the counter electrode increases, but remains a stable value. Therefore, the counter electrode of this embodiment can be used with an electrode area smaller than that of the counter electrode of the comparative example, and such electrode area is sufficient to support the electron flow through the working electrode, so that there is no bottleneck effect.

It should be noted that there is a significant signal difference between the counter electrode of the present embodiment and the counter electrode of the comparative example. Under the high concentration situation, the working electrode has a large amount of trivalent iron ions ($Fe^{3+}$) for its electroreduction. In contrast, the counter electrode of the comparative example does not oxidize the same amount of conductive dielectric at the same time, so the signal obtained is less than that of the counter electrode of the present example. The counter electrode of the present embodiment is self-oxidizable and can release electrons by oxidizing itself. In addition, the counter electrode of the present embodiment can also oxidize bivalent iron ions ($Fe^{2+}$). In this way, it is possible to provide a flow of electrons sufficient to match the flow of electrons on the working electrode, so that there is no bottleneck effect.

Figure 11A:
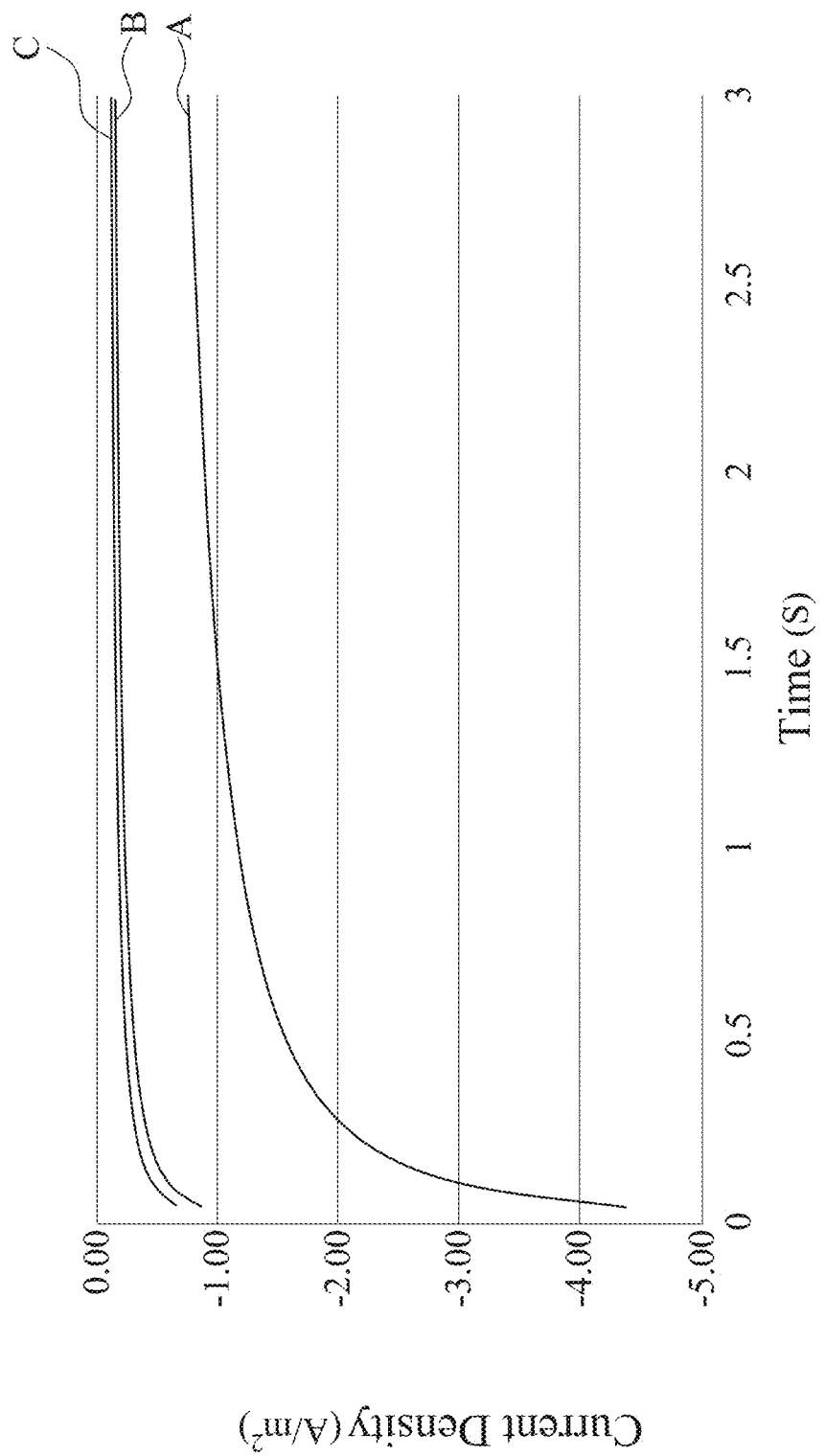
FIG. 11A and FIG. 11B are charts respectively showing the signals detected on an anode counter electrode and a cathode counter electrode with different materials.
Figure 11B:
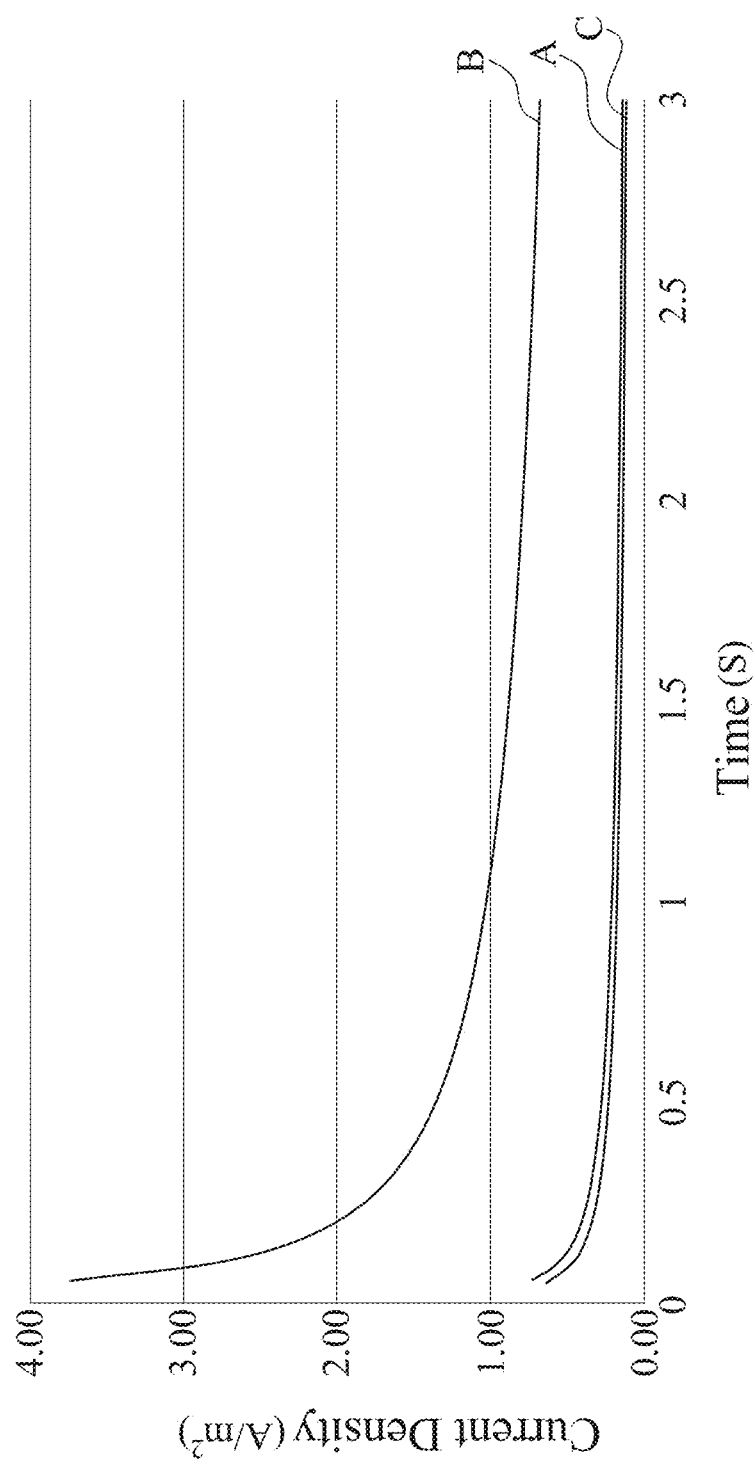

FIG. 11A and FIG. 11B are charts respectively showing the signals detected on an anode counter electrode and a cathode counter electrode with different materials. The working electrode is a carbon electrode, the counter electrodes are made of three different materials, including silver (Curve A), silver oxide (AgO) (Curve B) and carbon (Curve C), respectively, and the same chemical condition is used to measure the current density of ($A/m^2$) of the biochemical test chip.

As shown in FIG. 11A, the counter electrode in FIG. 11A is the anode. Carbon cannot undergo self-oxidization or self-reduction, so the level of the signal is related to the reactive layer and the area. Silver can undergo self-oxidization, and when the system environment satisfies the equation of $E_s^0 < E_m^0 - E_v$, silver is self-oxidized, and hence, its current density is greater than that of the carbon. Silver oxide cannot undergo self-oxidization; hence, when the counter electrode is the anode, even when the system environment satisfies the equation of $E_s^0 < E_m^0 - E_v$, it is not possible to oxidize silver oxide to provide electrons, and hence, its current density ($A/m^2$) is similar to that of the carbon electrode.

It should be noted that the active material of the present disclosure refers to the material that undergoes a secondary reaction when the counter electrode is an anode and the system satisfies the equation of $E_s^0 < E_m^0 - E_v$; however, the present disclosure does not limit to the embodiments where the secondary reaction can increase the current density. In some embodiments, the current density of the counter electrode is greater than twice of the current density of the working electrode. Moreover, the present disclosure does not limit the condition of the counter electrode when in use; for example, the counter electrode may comprise the active material as manufactured or may possess the functionality of the active material through the measuring apparatus. In some embodiments, the counter electrode can be silver oxide, and after the specimen is loaded into the reaction zone, an appropriate the potential is applied to reduce the silver oxide into silver.

As shown in FIG. 11B, the counter electrode in FIG. 11B is a cathode. In the present embodiment, silver without reduction capability cannot receive additional electrons, and hence it cannot undergo the secondary reaction when the system environment satisfies the condition of $E_s^0 > E_m^0 - E_v$, so the current density (A/m2) of silver is similar to that of carbon. In contrast, silver oxide has reduction capability and can undergo the secondary reaction when the system environment satisfies the condition of $E_s^0 > E_m^0 - E_v$, and hence, the current density (A/m2) of silver oxide is higher than that of silver.

As discussed above, the active material of the present disclosure refers to materials capable of undergoing secondary reaction in a condition matching the polarity of the counter electrode. In other words, even though the active material can be self-oxidized or self-reduced under specific environment, when the primary reaction is taking place, if the environment of the primary reaction cannot oxidize or reduce the active material, then such active material is not suitable to be used as the counter electrode of the present disclosure.

The above description of the present disclosure provides a variety of biochemical test chips with a counter electrode including an active material, including a counter electrode with an active material that can provide an amount of electrons equivalent to the amount of electrons generated by the conductive medium reaction on the working electrode when the electrode area is limited or the concentration of conductive medium on the surface of the counter electrode in the reaction solution is not high, and a suitable voltage is applied to the system, thereby enhancing the electroneutrality of the counter electrode and stabilizing the electrochemical circuit without current bottleneck effects. In some embodiments, the biochemical test chip further includes a protective layer to aid in the stability of the active material on the electrode, thereby protecting the biochemical test chip and slowing or avoiding unintended spoilage of the biochemical test chip due to reaction with the environment.

Although the disclosure and its advantages have been described in detail, it should be understood that various modifications, substitutions and replacements can be made without departing from the spirit and scope of the present disclosure as defined by the appended claims. In addition, the scope of the present application is not limited to specific examples of processes, machines, manufactures, material components, means, methods and procedures described in the specification. Those skilled in the art can understand from the disclosure of the present application that existing or future developed processes, machinery, manufacturing, and materials that have the same functions or achieve substantially the same results as the corresponding embodiments described herein can be used according to this disclosure. Accordingly, such process, machine, manufacture, material composition, means, method, or step fall within the protection scope of the present application.

What is claimed is:

1. A biochemical test chip, comprising:
   an insulating substrate;
   an electrode unit, located on the insulating substrate, wherein the electrode unit comprises a working electrode and a counter electrode, wherein a current density of the counter electrode is greater than a current density of the working electrode;
   a first insulating septum, located on the electrode unit, wherein the first insulating septum has an opening, and the opening at least partially exposes the electrode unit;
   a reactive layer, located at the opening and electrically connected to the electrode unit; and
   a second insulating septum, located on the first insulating septum;
   wherein the reactive layer and a target analyte undergo a primary reaction, and the counter electrode is configured to undergo a self-redox reaction, wherein the self-redox reaction does not interfere with the primary reaction, and the self-redox reaction allows the counter electrode to have the capability of receiving or releasing additional electrons;
   wherein the counter electrode is a cathode, and a standard reduction potential of an active material of the counter electrode satisfies $E_s^0 > E_m^0 - E_v$, where the $E_s^0$ is the standard reduction potential of the active material, the $E_m^0$ is a standard reduction potential for concentration reaction on the working electrode, and the $E_v$ is a potential applied by a measuring apparatus when providing measuring reaction.

2. The biochemical test chip of claim 1, wherein the current density of the counter electrode is greater than or equal to twice of the current density of the working electrode.

3. The biochemical test chip of claim 1, wherein an area of the counter electrode is smaller than or equal to an area of the working electrode.

4. The biochemical test chip of claim 1, wherein the counter electrode comprises a first portion and a second portion, wherein the first portion and the reactive layer do not overlap with each other.

5. The biochemical test chip of claim 1, wherein the counter electrode comprises a first portion and a second portion, and the opening at least partially exposes the first portion.

6. The biochemical test chip of claim 1, further comprising a protective layer, electrically connected to the electrode unit.

7. The biochemical test chip of claim 1, wherein the electrode unit further comprises a second counter electrode, wherein the counter electrode and the second counter electrode are separated from each other.

8. The biochemical test chip of claim 7, wherein a standard reduction potential of the counter electrode is greater than a standard reduction potential of the second counter electrode.

9. The biochemical test chip of claim 7, wherein a sum of an area of the counter electrode and an area of the second counter electrode is smaller than or equal to an area of the working electrode.

* * * * *